United States Patent [19]

Kim et al.

[11] Patent Number: 5,648,225

[45] Date of Patent: Jul. 15, 1997

[54] METHOD OF USING A MULTI-PURPOSE REAGENT FOR SUBCLASSIFICATION OF NUCLEATED BLOOD CELLS

[75] Inventors: Young Ran Kim, Sunnyvale; Johanna Kantor, Palo Alto; James E. Gill, Mountain View; Sue E. Luptovic, San Jose, all of Calif.

[73] Assignee: Abbott Laboratories, Abbott Park, Ill.

[21] Appl. No.: 296,379

[22] Filed: Aug. 25, 1994

Related U.S. Application Data

[62] Division of Ser. No. 23,042, Feb. 25, 1993, abandoned.

[51] Int. Cl.$^6$ .................................................... G01N 33/49
[52] U.S. Cl. .................. 435/7.24; 435/7.25; 436/536; 436/548; 436/17; 436/63; 436/166; 436/172; 436/174; 436/805; 424/154.1; 424/93.71; 424/93.73
[58] Field of Search .............................. 436/10, 17, 18, 436/63, 130, 166, 805, 536, 546, 548, 172, 174; 435/2, 7.24, 7.25; 424/154.1, 93.71, 93.73

[56] References Cited

U.S. PATENT DOCUMENTS

| | | |
|---|---|---|
| 4,284,412 | 8/1981 | Hansen et al. . |
| 4,637,986 | 1/1987 | Brown et al. . |
| 4,654,312 | 3/1987 | Chang et al. . |
| 4,656,139 | 4/1987 | Matsuda et al. . |
| 4,745,071 | 5/1988 | Lapicola et al. . |
| 4,751,179 | 6/1988 | Ledis et al. . |
| 4,801,549 | 1/1989 | Cremins et al. . |
| 4,902,613 | 2/1990 | Chang et al. . |
| 4,971,917 | 11/1990 | Kuroda et al. . |
| 4,978,624 | 12/1990 | Cremins et al. . |
| 4,985,174 | 1/1991 | Kuroda et al. . |
| 5,047,321 | 9/1991 | Loken et al. . |
| 5,098,849 | 3/1992 | Hilerio et al. . |
| 5,125,737 | 6/1992 | Rodriguez et al. . |
| 5,141,855 | 8/1992 | Schmittou . |
| 5,155,044 | 10/1992 | Ledis et al. . |
| 5,188,935 | 2/1993 | Leif et al. . |
| 5,232,857 | 8/1993 | LeFevre et al. . |
| 5,298,426 | 3/1994 | Inami et al. . |
| 5,486,477 | 1/1996 | Carver, Jr. . |

OTHER PUBLICATIONS

Loeffler et al. *Cytometry* 13:169–174 (1992), "Analysis of Distribution of Tumor–and . . . ".

H.M. Shapiro, et al., Combined Blood Cell Counting and Classification With Fluorochrome Stains and Flow Instrumentation, *The Journal of Histochemistry and Cytochemistry*, vol. 24, No. 1, pp. 396–411 (1976).

Leon W.M.M. Terstappen, et al., Five-Dimensional Flow Cyotmetry as a New Approach for Blood and Bone Marrow Differentials, *Cytometry*, 9:548–556 (1988).

*Primary Examiner*—Paula K. Hutzell
*Assistant Examiner*—Rachel Heather Freed
*Attorney, Agent, or Firm*—Nicholas A. Poulos

[57] ABSTRACT

A multipurpose reagent system for rapid analysis of a whole blood sample allowing the determination of at least five classes of peripheral white blood cells, nucleated red blood cells, and lymphocyte immunophenotyping on automated hematology instrumentation. The multipurpose reagent system lyses red cells rapidly, while it concurrently fixes white cells and preserves surface antigens on lymphocytes. The multipurpose reagent system comprises from about 3 to 7 grams per liter of a non-quaternary ammonium salt, from about 0.04 to about 0.10 percent by volume of an aliphatic aldehyde with one to four carbons, from about 10 mM to about 20 mM of a non-phosphate buffer which is inert to the aliphatic aldehyde, and a sufficient amount of water to give a pH between 5.5 and 7.5 and an osmolality of between about 160 to about 310 mOsm per liter.

10 Claims, 16 Drawing Sheets

METHOD OF USING A MULTI-PURPOSE BEAGENT FOR SUBCLASSIFICATION OF NUCLEATED BLOOD CELLS

This is a divisional application of application Ser. No. 08/023,042, filed Feb. 25, 1993, now abandoned.

BACKGROUND

This invention relates to a multipurpose reagent system and a method for a rapid analysis of whole blood samples. More particularly, the present invention relates to a multi-purpose reagent system capable of rapidly lysing red cells and concurrently fixing white cells, useful for performing white cell differential analyses and quantitative analyses of nucleated red blood cells or lymphocyte subclassification using immunophenotyping techniques on an automated clinical hematology analyzer or flow cytometer.

The peripheral blood of a normal subject contains red blood cells, also known as erythrocytes, and five major classes of mature white cells, also known as leukocytes. There are at least five classes of leukocytes, known as neutrophils, eosinophils, monocytes, lymphocytes and basophils. Each type of mature blood cell performs specialized functions necessary in maintaining the homeostasis of the host. The concentration of each class of peripheral blood cells is tightly regulated and monitored by a dynamic process involving a variety of factors present in the microenvironment of the bone marrow. Under certain disease conditions, the bone marrow may release either an increased or decreased number of certain classes of white cells. In other conditions, all regulation of the number of peripheral blood cells released from the bone marrow is perturbed and an uncontrolled number of immature white or red cells are released to the peripheral blood.

Therefore, monitoring the concentration of the five normal classes of leukocytes and identifying the presence of immature erythrocytes and leukocytes in the peripheral blood is an important diagnostic tool for physicians. Typically, these functions have been performed by doing white cell differential counts, whereby the relative proportions of the five normal classes of leukocytes and any abnormal cells are determined microscopically. The manual procedure is very time consuming, subjective and labor intensive.

Recently, automated processes and automated flow system apparatuses have been developed to ease the burden of white cell differential analysis. Several of these systems are described in U.S. Pat. Nos. 4,099,917; 4,617,275; 4,521,518; and 4,801,549. Some of these systems are based on cytochemical procedures to specifically identify individual cell types; some of these systems differentiate three leukocyte types by electronic impedance measurements of cell volume; and other procedures utilize a combination of optical and electronic impedance measurements to differentiate the five classes of peripheral white blood cells.

Recent advances in cellular immunology and flow cytometry are being utilized to identify and quantify lymphocyte subclasses such as helper T cells. Lymphocyte subclassification has become an important diagnostic tool, particularly in view of the growing AIDS epidemic. Conventional lymphocyte subclassification involves the following steps: (1) The separation of lymphocytes from other peripheral blood cells by density gradient centrifugation; (2) the reaction of the lymphocytes with fluorochrome-labeled monoclonal antibodies directed to specific lymphocyte surface antigens; and (3) the analysis of lymphocyte-antibody reaction products using flow cytometry. Currently, a great deal of effort is being directed towards the development of whole blood methods that bypass the need for density gradient centrifugation. Recently developed whole blood methods for lymphocyte subclassification comprises lysing the red cells, removing red cell ghosts and cell debris by centrifugation, and preserving the morphology of the remaining white cells by suspending the white cells in an isotonic saline solution containing appropriate fixatives. Although these methodologies avoid the need for density gradient centrifugation, they are still incompatible with available automated clinical hematologic analyzers since they still require a centrifugation step.

Generally speaking, the reagent systems available for use during the analysis of nucleated red blood cells (NRBC) are as yet unable to allow for the differentiation and counting of NRBC signals from red cell stroma or large platelets and only allow the instrument to flag possible NRBC signals.

It is imperative in leukocyte analyses that all of the red blood cells be completely lysed. Since red cells outnumber white cells by about 700 to 1, even one percent of unlysed red cells may distort white cell counts. Some reagents used to lyse red cells require too lengthy an incubation period to be practical in an automated clinical analyzer. For example, the Tris buffered ammonium chloride solution recommended by K. A. Murihead in *Clinical Cytometry*, Ann. N.Y. Acd. Sci., vol. 468, pp. 113–127 (1986) takes 5 to 10 minutes to lyse red cells, which is too impractical for automation.

Furthermore incomplete hemolysis with certain lytic reagents can result in red cell stroma that retain sufficient hemoglobin to generate high background counts in automated clinical electro-optical systems. Therefore, the white cells to be analyzed must first be removed from the red cell stroma by centrifugation, a procedure that is a limiting factor when adapting a reagent system for automation.

Other reagent systems, such as those described in U.S. Pat. Nos. 4,902,613 and 4,654,312, that are used to lyse red cells, contain high refractive index solvents. A cell suspending medium which has a high refractive index has two disadvantages: (1) The refractive index may be too high for a common flow cell saline sheath; and (2) the high refractive index of the suspending medium may mask signals from small cellular components such as small lymphocytes and cytoplasm-lysed nucleated red cells. Thus, before the cells can be analyzed in a flow cell, the cells must be removed from the high refractive index medium by centrifugation and resuspended in an isotonic solution. Such manual procedures are not desirable or adaptable for use on a fully automated clinical analyzer.

In addition, lytic reagents, such as those described in U.S. Pat. No. 5,155,044, are too hypotonic and/or acidic. Such lysing reagents require the rapid "follow-up" addition of a high salt solution and/or alkaline salt solution to preserve the white cell morphology for analysis. Similarly, lytic reagents, such as those described in U.S. Pat. No. 4,751,179, will not only lyse red cells but will also lyse white cells, unless a separate fixative is added at the appropriate time and concentration to prevent white cell lysis. These reagents introduce the potential of white cell damage, particularly in abnormal blood samples containing fragile white cells (such as in blood samples from patients with chronic lymphocytic leukemia [CCL]).

Furthermore, reagent systems, such as those described in U.S. Pat. Nos. 4,099,917, 4,801,549, and 4,978,624, require incubations at high temperatures, e.g. over 50° C., to completely lyse the red cells. Temperatures over 45° C. will, generally, begin to denature most cell surface antigens and cause hemoglobin clumping in the process. Although these systems may be used to perform differential analyses of white cells, they destroy the means for differentiating subpopulations of lymphocytes and cannot be used for immunophenotypic lymphocyte classification.

Many of the currently used reagent systems require the cytochemical staining of fixed white cells before they are subjected to differential analysis. These systems require the timed addition of multiple reagents and incubation periods and are generally not adaptable for the quantitation of nucleated red cells or for immunophenotypic lymphocyte classification. Furthermore, each step of reagent addition or other manipulation of a blood sample decreases the precision of the final counts obtained from that sample.

Based on the foregoing, a need has arisen for a multipurpose reagent system which can lyse red cells rapidly and completely, while concurrently preserving white cell morphology and lymphocyte cell surface antigens.

SUMMARY

The problems discussed above have been solved in the present invention.

Accordingly, an object of the present invention is to provide a multipurpose reagent system, or blood diluent, that will lyse red cells rapidly and completely, while concurrently preserving white cell morphology and lymphocyte cell surface antigens for the automated electro-optical analyses of peripheral whole blood cells.

Another object of the present invention is to provide a multipurpose reagent system that permits the rapid differentiation of white cells on an automated clinical hematologic analyzer.

Still another object of the present invention is to provide a multipurpose reagent system which permits the identification and quantitation of nucleated red blood cells (NRBCs) on an automated clinical hematologic analyzer.

Yet another object of the present invention is to provide a multipurpose reagent system that eliminates the necessity of centrifuging lymphocyte-antibody reaction products prior to the enumeration of fluorochrome conjugated antibody bound lymphocyte subclasses on an automated clinical flow cytometer.

The multipurpose reagent system of the present invention is comprised of a non-quaternary ammonium salt, an aliphatic aldehyde having one to four carbons, a non-phosphate buffer substantially inert to the aliphatic aldehyde, and water to give an effective pH of between about 5.5 and about 7.5 and an osmolarity of between about 160 to about 310 mOsm/L (milliosmols per liter). Various optional reagents for the present invention include a surface active agent such as saponin, an anticoagulant, an alkali salt of bicarbonate, a nuclear stain, or an antibody directed against specific cell surface antigens.

One method of the present invention comprises preparing a multipurpose reagent system, mixing the multipurpose reagent system with a whole blood sample, incubating the reagent system-blood mixture for at least 10 seconds, and analyzing the blood sample on an automated hematology analyzer.

One feature and technical advantage of the present invention is that the disclosed multipurpose reagent system can rapidly and completely lyse red blood cells while concurrently preserving white cell morphology, while, eliminating the need for the addition of a second reagent or fixative. The disclosed process of red cell lysis can take place in less than 20 seconds.

Another feature and technical advantage of the present invention is that the disclosed multipurpose reagent system fixes white cells adequately and will not lyse fragile lymphocytes such as CLL lymphocytes. Further, the multipurpose reagent system has been shown to stabilize white cells exposed to the reagent over extended periods of time.

Still another feature and technical advantage of the present invention is that the disclosed multipurpose reagent system has a refractive index similar to that of isotonic saline, used in other hematologic measurements.

Another feature and technical advantage of the present invention is that the lysing power of the disclosed multipurpose reagent system is potent enough to completely and rapidly lyse red cells in as low as a 16-fold diluted whole blood sample, thus retaining sufficient white cell density to allow accurate and rapid cell analysis. This allows for automated analysis in a multi-parameter clinical instrument.

Still another feature and technical advantage of the present invention is that the disclosed multipurpose reagent system preserves lymphocyte cell surface antigens, for example, CD3, CD4, CD8, and CD19.

Yet another feature and technical advantage of the present invention is that the disclosed method lyses red blood cells so thoroughly that signals from red cell ghosts are sufficiently small to be clearly separated from those of lymphocytes without washing or otherwise removing the red cell stroma while still providing improved subpopulation separation.

Yet another feature and technical advantage of the present invention is that the disclosed method of peripheral blood analysis bypasses the need for either conventional or density gradient centrifugation steps.

Still yet another feature and technical advantage of the present invention is that the disclosed method permits the quantification of nucleated red blood cells on a clinical flow cytometer.

A further feature and technical advantage of the present invention is that the disclosed multipurpose reagent system enables a rapid, one-reagent, one-tube, automated differential analysis of peripheral white blood cells.

An additional feature and technical advantage of the present invention is that method allows for a rapid differential analysis of lymphocyte subclasses on an automated flow cytometer.

These and further features and advantages of the invention will be apparent from the following description of the preferred embodiments thereof.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
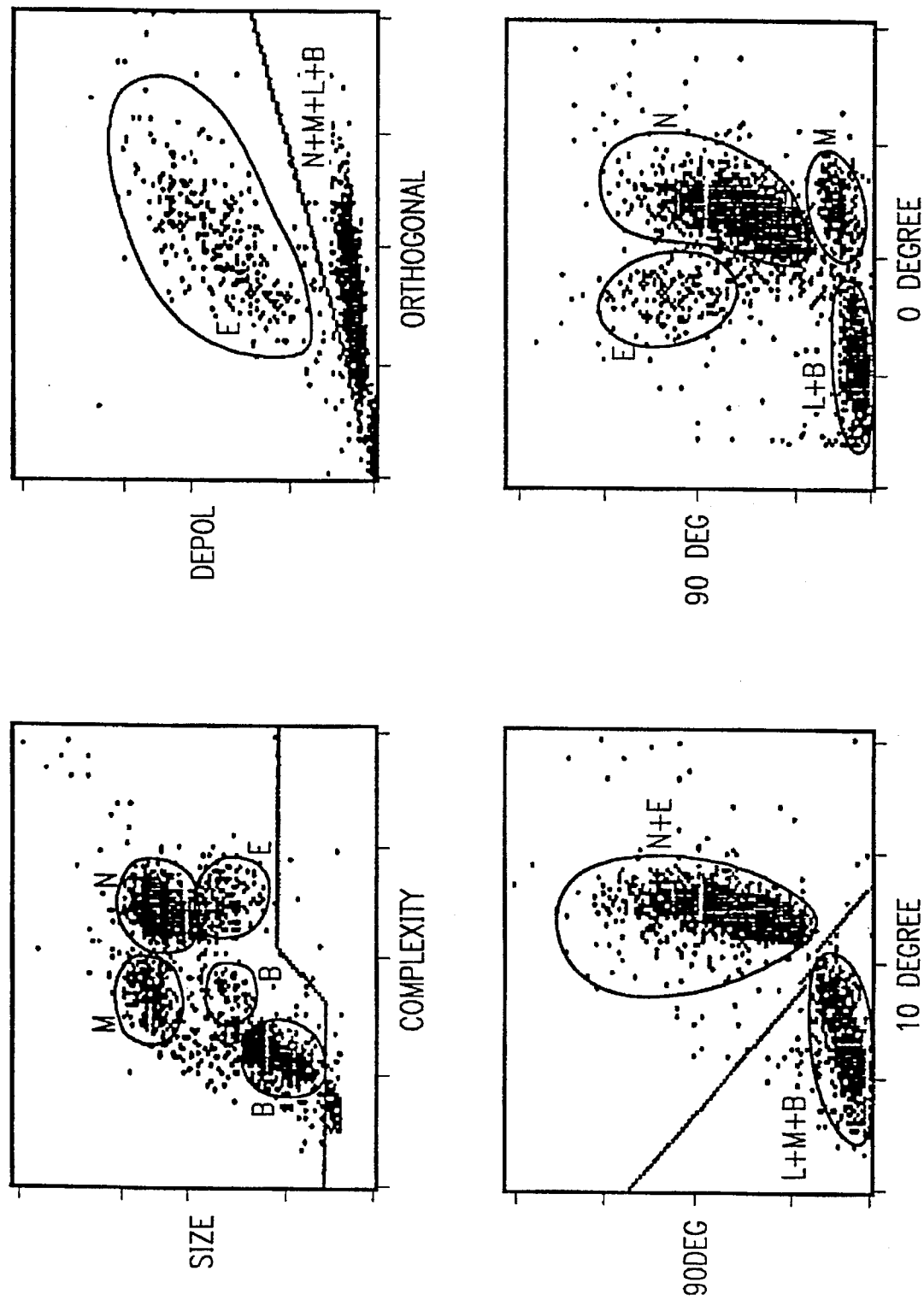
FIG. 1 shows the white cell distribution of a normal blood sample processed as described in Example 1. The prepared cell suspension was run directly through a CD3500™ analyzer optical system bypassing the system's hydraulics.

Broadly, the present invention relates to a multipurpose reagent system, or blood diluent, suitable for the rapid analysis of nucleated peripheral blood cells. The multipurpose reagent system can completely and rapidly lyse red blood cells, while concurrently preserving white cell morphology and the antigenicity of lymphocyte surface antigens.

One aspect of the present invention is the multipurpose reagent system, comprising of from about 3 to about 7 grams per liter of a non-quaternary ammonium salt, from about 0.04 to about 0.1% by weight volume (i.e., grams per 100 ml) of an aliphatic aldehyde with one to four carbons, from about 10 to about 20 mM of a non-phosphate buffer which is substantially inert to the aliphatic aldehyde, and water. The pH of the reagent system is within a pH range of about 5.5 to about 7.5 and the osmolality of the reagent system is between about 160 to 310 mOsm/L. The refractive index of the reagent system can be similar to that of saline and would be within the range of about 1.333 to about 1.336. The non-phosphate buffer which does not contain any primary amino group is inert to the aliphatic aldehyde. Thus, generally, the non-phosphate buffer should not contain a primary amino group.

A preferred embodiment of the present invention utilizes a multipurpose reagent system comprised of about 95 mM ammonium chloride (5 g/l), about 0.075% by volume of formaldehyde, from about 10 mM to about 20 mM acetate buffer, about 10 mM potassium bicarbonate, and about 0.01% by weight volume (i.e., grams per 100 ml) of saponin. The pH of the reagent system is adjusted to a range of from about 6.2 to about 6.5 and the osmolality of the reagent system is from about 215 to about 270 mOsm/L.

Osmolality is defined as the number of dissolved particles in a unit volume of an aqueous solution. Osmolarity is defined as the number of dissolved particles in a unit weight of water solution. As a practical matter, osmolality and osmolarity have numerical values which are very close in the ranges involved in the present invention. A solution that has 1/1000 of an osmol dissolved per kilogram has a concentration of 1 milliosmos ("mOs") per kilogram. An osmol is the number of particles in 1 gram molecular weight of undissociated solute. Tonicity is a measure of the osmotic pressure of a solution relative to the osmotic pressure of the blood fluids. A hypotonic solution is a solution of lower osmotic pressure of tonicity than that of blood. The osmolality of a hypotonic solution is usually in the range of about 80–250 mOs/l. An isotonic solution has the same tonicity as blood. Here, the osmolality usually ranges from about 280 to about 310 mOs/l. A hypertonic solution is a solution of greater tonicity than blood which normally has an osmolality range of about 310–440 mOs/l. Water has the osmolality of about 10–20 mOs/l.

The present invention also pertains to the use of the multipurpose reagent system in the automated determination of differential white cell counts, nucleated red blood cells, and lymphocyte immunophenotyping. The method for the rapid analysis of nucleated peripheral whole blood cells includes the following steps: mixing the multipurpose reagent system of the present invention with an anticoagulated whole blood sample (whereby the blood is diluted 16 to 100 fold), incubating the diluent-blood mixture at temperatures from about 25° C. to 46° C. for at least 10 seconds, and analyzing the nucleated peripheral blood cells with automated hematology instrumentation.

The method using the multipurpose reagent system of the present invention in the differential analysis of peripheral white blood cells is a rapid, one-reagent method of concurrently lysing red blood cells and fixing white blood cells, wherein the white cells maintain their light scattering characteristics. Example 1 illustrates the application of a preferred embodiment of the disclosed multipurpose reagent system in a rapid process for white cell differential analysis. FIG. 1 shows the differential analysis of white cells in a normal blood sample (processed as described in Example 1) by light scattering. In general, the cells flow through an optical view chamber where a photoelectric measuring process records the light absorbed or type of light scattered by each cell at selected angles. Electronic signals, from scattered light collected at different angles, are plotted as two dimensional dot plots as illustrated in FIG. 1. Granulocytes are identified first on the cytogram, 10 deg vs 90 deg scatter plot, by drawing the threshold between the granulocytes and the rest of the white cell population as shown in FIG. 1c. Eosinophils are identified next on the ORTHOGONAL vs DEPOL cytogram as shown in FIG. 1b. Then, monocytes and lymphocytes are identified on the SIZE vs COMPLEXITY cytogram (FIG. 1a) along the Y axis because monocytes are larger than lymphocytes. The signals that fall between lymphocytes and granulocytes along the X axis (COMPLEXITY) and which are lower than that of monocytes along the Y axis that do not belong to any of the populations already identified (neutrophils and eosinophils) are basophils, as labeled (FIG. 1a).

A first ingredient of the multipurpose reagent system is a non-quaternary ammonium salt. Preferably, neither di- nor tri-ammonium salts should be used. A variety of mono-ammonium salts, particularly the halogenated salts, can be used from about three to about seven grams per liter, and preferably at 5 grams per liter. Examples of such non-quaternary ammonium salts include $NH_4X$, where X is a halogen. Preferably, such a non-quaternary ammonium salt is $NH_4Cl$.

A second ingredient of the multipurpose reagent system is a short-chain aliphatic aldehyde. Preferably, such aliphatic aldehydes have from one to four carbons. Exemplary aldehydes include formaldehyde and the polymer, paraformaldehyde. In proper ratios and concentrations, the aldehyde, in conjunction with the non-quaternary mono-ammonium salt, and the buffer, will rapidly and completely lyse the red blood cells. In addition, the aldehyde will fix white blood cells and preserve their membrane integrity. Formaldehyde, or comparable aldehyde, will be present in the present invention in amounts from about 0.04% to about 0.10% by volume, and preferably from about 0.08% to about 0.1% by volume.

A third ingredient of the multipurpose reagent system is a non-phosphate buffer that is substantially inert to the aldehyde component of the reagent system. Thus, the buffer must not contain a primary amino group. The buffer should also have an effective buffering capacity between pH of about 5.5 and about 7.5. Examples of effective organic buffers are acetate buffer, succinate buffer, maleate buffer, and citrate buffer. Examples of effective biologic buffers are 2-(N-morpholine)ethane sulfonic acid (MES) buffer, 3-(N-morpholine)propane sulfonic acid (MOPS) buffer, and N-(2-hydroxyethyl)piperazine-N'-(2-ethane sulfonic acid) (HEPES) buffer. An acetate, or other suitable buffer, will be present in the present invention in amounts from about 10 mM to about 20 mM concentrations, and preferably at about 20 mM concentration. Embodiments of the present invention using MES buffer, MOPS buffer, and HEPES buffer are described in Examples 6, 7, and 8, respectively.

An optional component of the multipurpose blood diluent is a surface active reagent. The preferred surface active agent is saponin, a plant extract that is available in a commercial grade powder isolated from quillaja tree bark as well as other sources. Although the chemical purity of commercial saponin varies from lot to lot, it is more selective towards red cells than are the quaternary ammonium salts. Saponin, or other surface active reagent, is present in the present invention in amounts from about 10 to about 200 mg/L, and preferably at about 100 mg/L. Saponin, in concert with the other ingredients of the multipurpose reagent system completely lyses the red blood cells present in whole blood. The erythrocyte fraction (i.e. red blood cells) of normal blood samples will be lysed within about 20 seconds at ambient temperatures. However, hard-to-lyse blood samples (such as blood samples from babies, kidney dialysis patients, multiple myloma patients, diabetics, or patients with uremia) require incubating the blood with the reagent system at temperatures of about 38° C. to about 43° C. for up to 20 seconds for complete erythrocyte lysis. Incubation of blood samples with the multipurpose reagent system, even at these slightly elevated temperatures, effectively preserves white cell membrane integrity and retains the antigenicity of lymphocyte surface antigens. In contrast, if saponin is used by itself to lyse the red cells, it must be used at a concentration 10 to 20 times higher than those used in the present invention. Such concentrations are extremely damaging to the integrity of the white cells and require a rapid quenching of the lytic activity of the reagent to preserve white cell morphology. An advantage of the present invention is that the combined constituents of the multipurpose reagent system serve to gently fix the white cells at the same time that the red cells are being lysed. Therefore, white cell integrity is preserved even at relatively long incubation periods. In fact even fragile white cells, such as those seen in chronic lymphocytic leukemia, are stabilized in the multipurpose reagent system of the present invention for incubation periods of up to 20 minutes.

Figure 2:
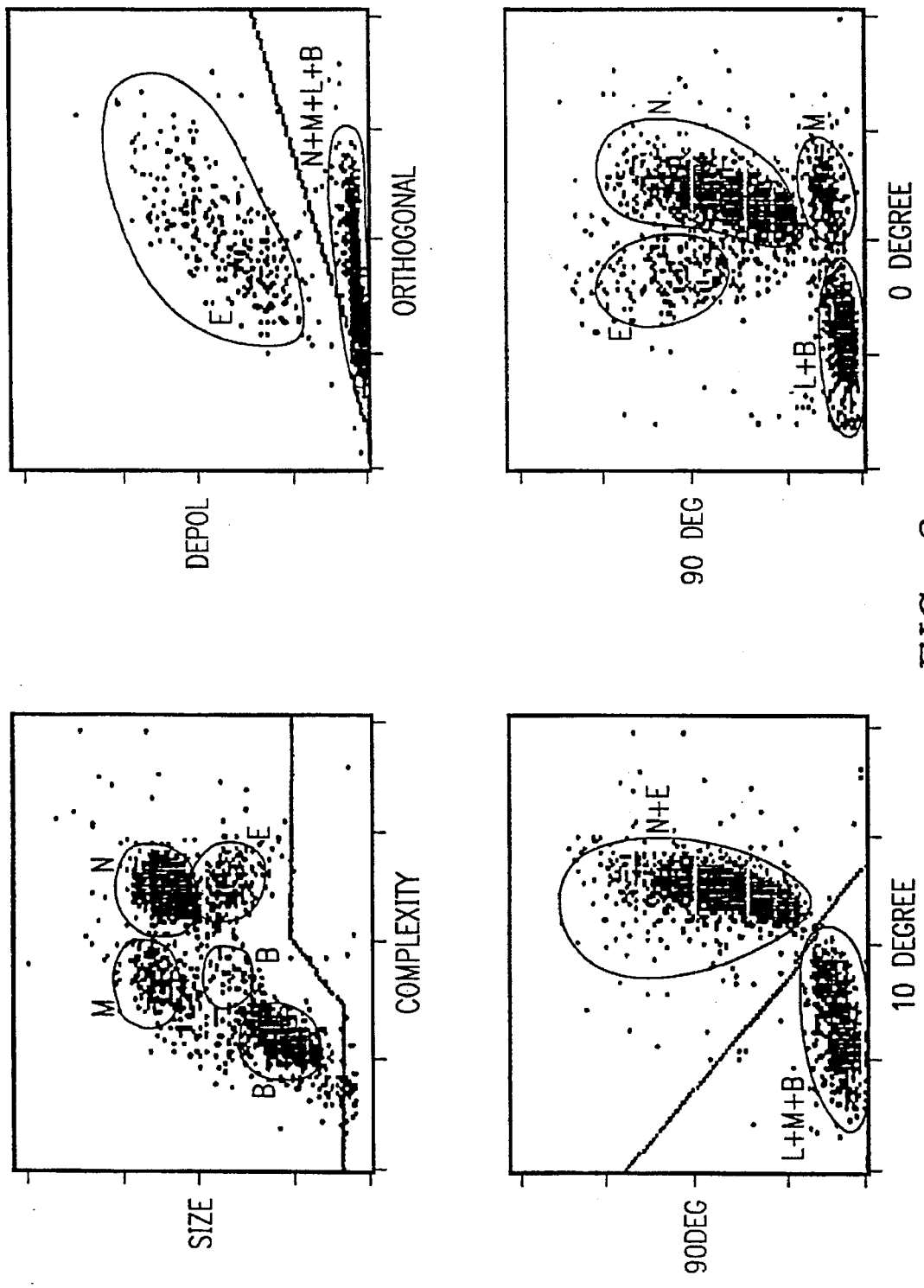
FIG. 2 shows the white cell distribution of a normal blood sample processed as described in Example 12. The processed cell suspension was run directly through a CD3500™ analyzer optical system bypassing the system's hydraulics. Each cluster represents a white cell subpopulation as labeled.

FIG. 2 shows the distribution of white cells in a normal blood sample processed as described in Example 12 and run on the CD3500™ analyzer (Abbott Diagnostic, Mountain View, Calif.) system directly through its optical system but bypassing the system hydraulics. Granulocytes are identified first from the rest of the white cell populations, as labeled, on the 10 deg vs 90 deg scatter plot, by setting the threshold as shown in FIG. 2c. Eosinophils are identified next on the ORTHOGONAL vs DEPOL scatter plot (FIG. 2b), as labeled, by setting the threshold between eosinophils and neutrophils as shown in FIG. 1b. Then, moHOCytes and lymphocytes are identified on the COMPLEXITY vs SIZE scatter plot, as labeled (FIG. 2a). The signals that fall between lymphocytes and granulocytes along the X axis (COMPLEXITY) and which are lower than that of monocytes along the Y axis that do not belong to any of the populations already identified (neutrophils and eosinophils) are basophils, as labeled (FIG. 2a).

A preferred but optional ingredient of the multipurpose reagent system according to the present invention is an alkali salt, preferably a monovalent alkali salt of bicarbonate. Although a monovalent alkali salt of bicarbonate is not an essential component of the diluent, it may be added to the diluent to raise its osmolality without reducing the red cell lysability of the reagent system. Many other compounds, such as sodium chloride, potassium chloride or phosphate buffer, will diminish the lysability of the reagent system if they are used to increase the osmolality of the reagent system. Exemplary monovalent alkali salts of bicarbonate are potassium bicarbonate, sodium bicarbonate, or lithium bicarbonate. Potassium bicarbonate, or other alkali bicarbonate salt, can be present in the present invention in amounts from about 0.005% to about 0.015% weight/volume (i.e. milligrams per 100 ml), and preferably at about 0.01% weight/volume.

Another optional ingredient of the multipurpose reagent system according to the present invention is a platelet anti-clumping agent. For example, an ethylenediaminetetraacetate (EDTA) salt can be added to the reagent system to prevent platelet aggregation in the sample/reagent mixture. Tetrasodium EDTA, of other EDTA salts, will be present in the present invention in amounts from about 20 to about 200 mgs per liter, and preferably at 100 mgs per liter.

Another embodiment of the present invention allows for the quantitative analysis of nucleated red cells on automated hematology analyzers. In order to analyze the percentage of nucleated red cells present in a whole blood sample, a nuclear stain, e.g., ethidium homodimer, is added to the multipurpose reagent system before it is added to the blood sample In this embodiment, the nuclear stain is added to the reagent system in an amount from between about 0.05 mg % to about 0.15 mg % weight/volume (i.e., milligrams per 100 ml), and preferably at 0.1 mg % weight/volume. The reagent system completely lyses the red cells while simultaneously preserving the integrity of white cell membranes. In the multipurpose reagent system, the added nuclear stain reacts with the exposed nuclei of immature red cells, yet it is impenetrable to intact white cells. Since the only nuclear material available to interact with the nuclear stain is that from the nucleated red blood cells, the stained nuclear material is proportional to the nucleated erythrocyte fraction of the blood sample and can be quantitated on an automated electro-optical analyzer. This one-reagent process of the present invention allows one to rapidly distinguish the different leukocyte populations from nucleated erythrocytes, and is particularly useful for certain veterinary applications.

Figure 3A:
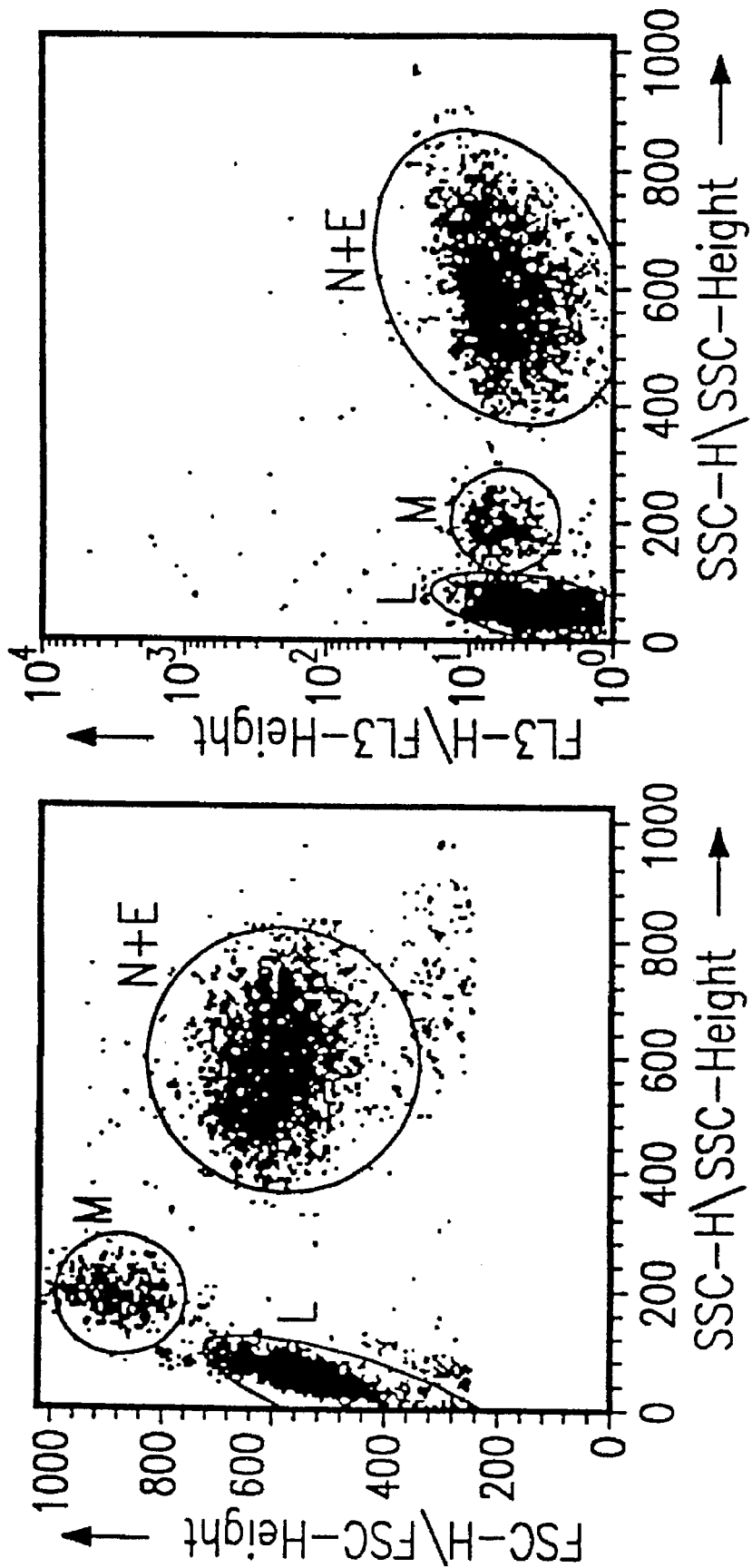
FIG. 3a shows a FACScan™ display printout of a normal blood sample, processed as described in Example 5 with a nuclear stain but without chicken erythrocyte nuclei (CEN)
Figure 3B:
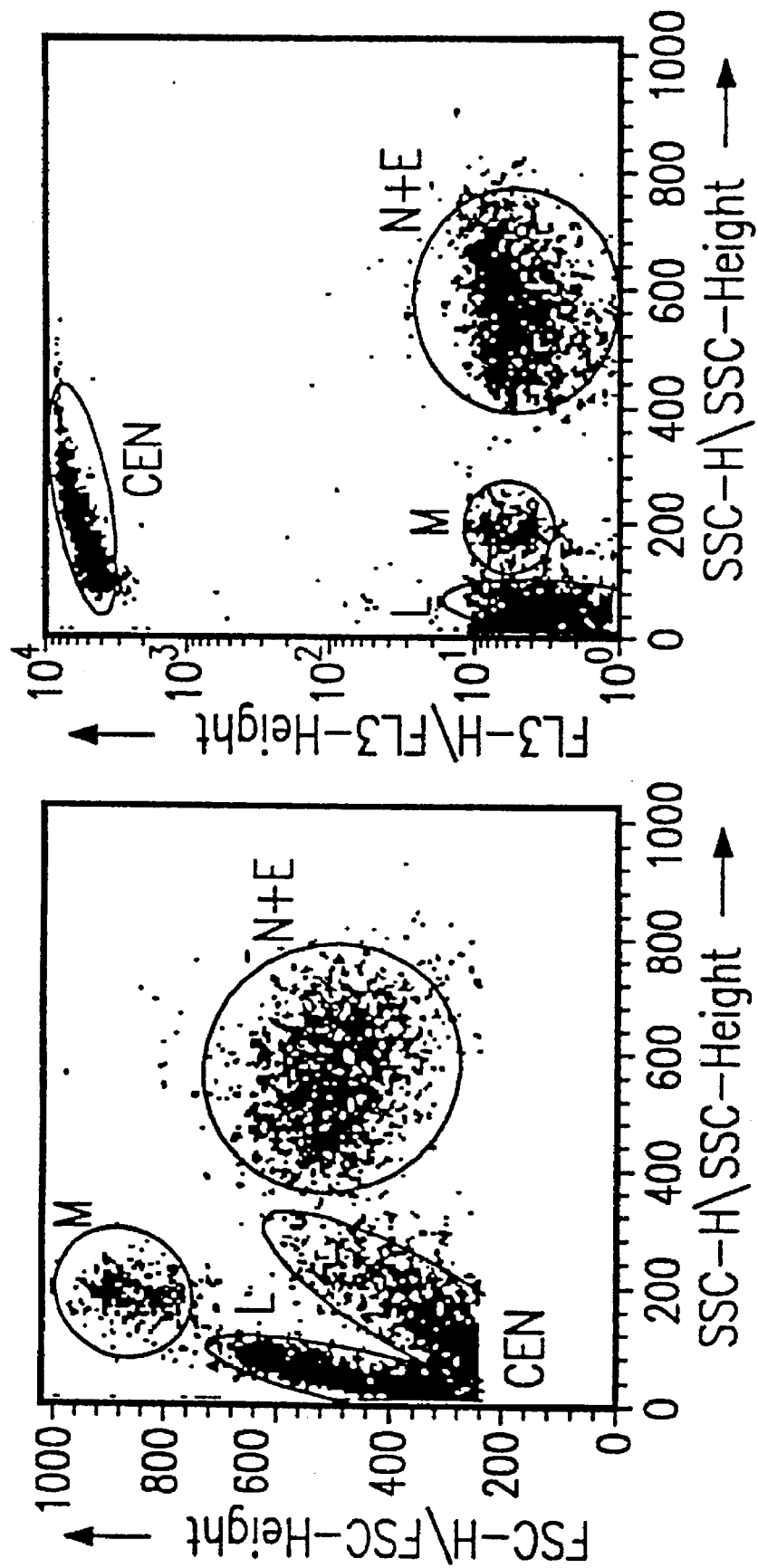
FIG. 3b shows a FACScan™ display printout of a normal blood sample, supplemented with chicken erythrocyte nuclei, that was processed as described in Example 5 with a nuclear stain. An FL3 stained CEN population appears at the upper left hand corner.

FIG. 3 shows a FACScan™ display of a normal blood sample with chicken erythrocyte nuclei (CEN processed as described in Example 5. The sample shown in FIG. 3a was processed with a nuclear stain but without CEN and the sample shown in FIG. 3b was processed in the presence of both a nuclear stain and CEN. The two dimensional dot plots on the left have plotted side scatter (SSC) versus forward scatter (FSC). The two dimensional dot plots on the right have SSC signals plotted versus red fluorescence (FL3) from all the cells in the sample. Note the appearance of a FL3 stained CEN population in FIG. 3b at the upper left corner.

A further embodiment of the present invention allows for the quantitative analysis of lymphocyte subpopulations.

Lymphocyte subclassification is achieved by mixing fluorochrome-conjugated monoclonal antibodies, directed to specific lymphocyte surface antigens, with whole blood samples before adding the multipurpose reagent system, or blood diluent. The concentration of labeled antibody fractions added to a blood sample will depend upon the individual antibody preparation, but is commonly about one-half to one-tenth of the volume of the blood for commercial antibody preparations. After the reagent system is added and the red cells are lysed, the lymphocyte-antibody reaction products can be analyzed on an automated flow cytometric system. The disclosed reagent system does not "quench" fluorescent markers, such as fluorescein isothiocyanate (FITC) or phycoerytherin (PE), which are frequently used to fluorochrome-label antibodies. Lymphocyte subclassification has become increasingly important as a diagnostic tool with the advent of the AIDS epidemic. The ability to identify surface markers on blood cell populations is likely to become increasingly important over the years as scientists increase their knowledge of surface components and characteristics of subpopulations of lymphocytes and other white cell fractions such as monocytes and neutrophils.

Figure 4A:
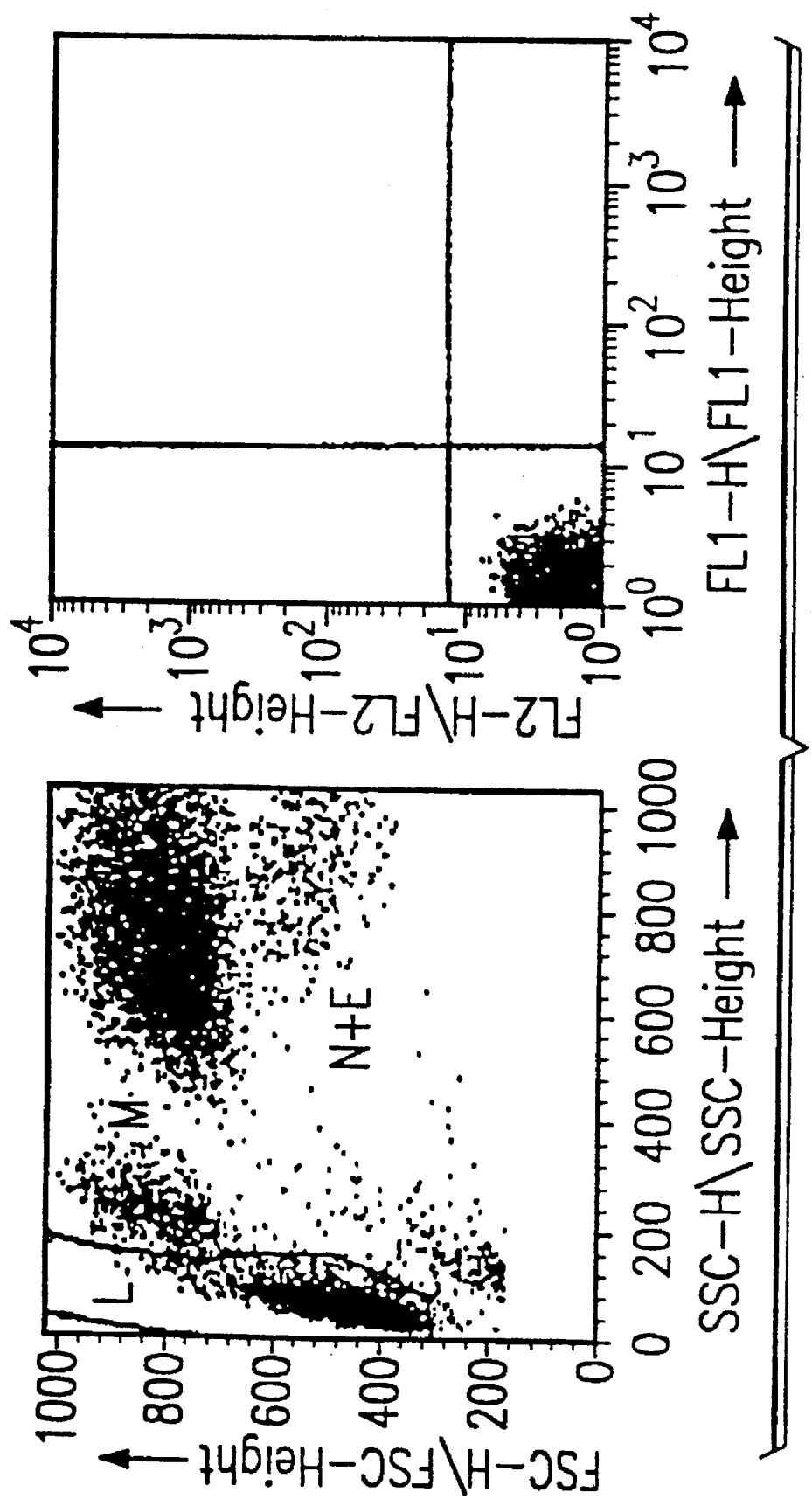
FIGS. 4a, 4b, 4c and 4d show FACScan™ display printouts of a normal blood sample processed as described in Examples 2, 3 and 4.
Figure 4B:
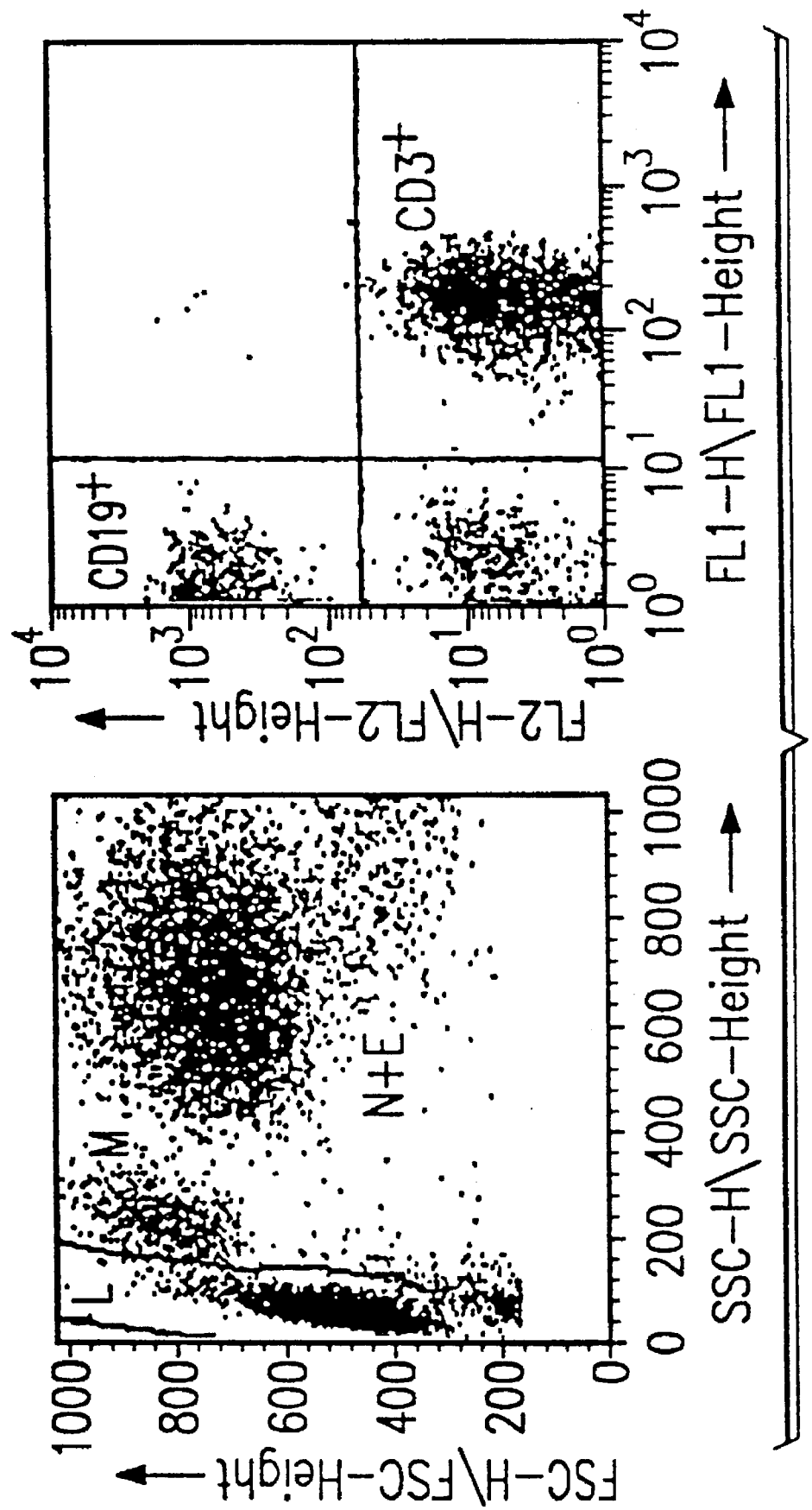
Figure 4C:
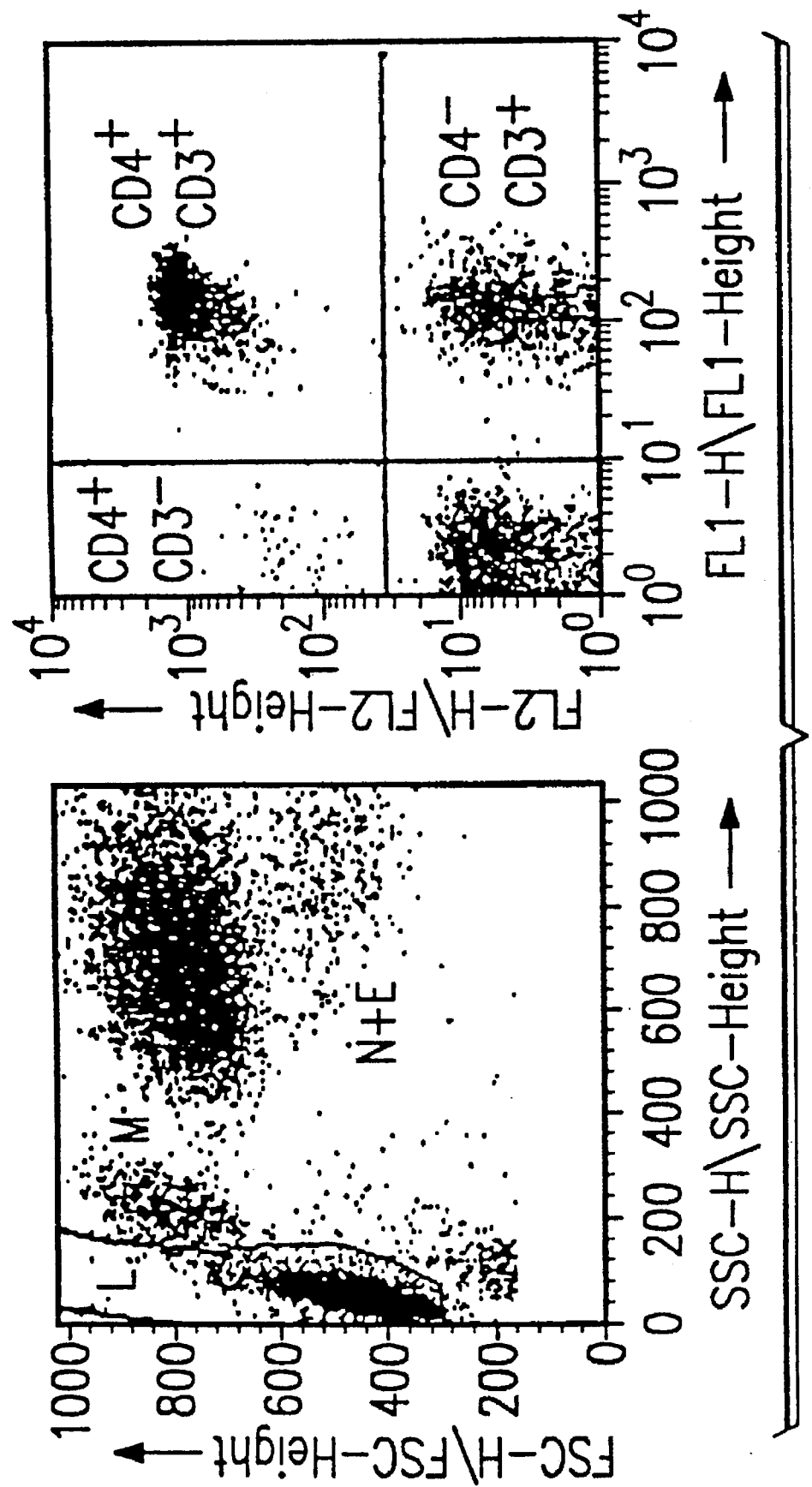
Figure 4D:
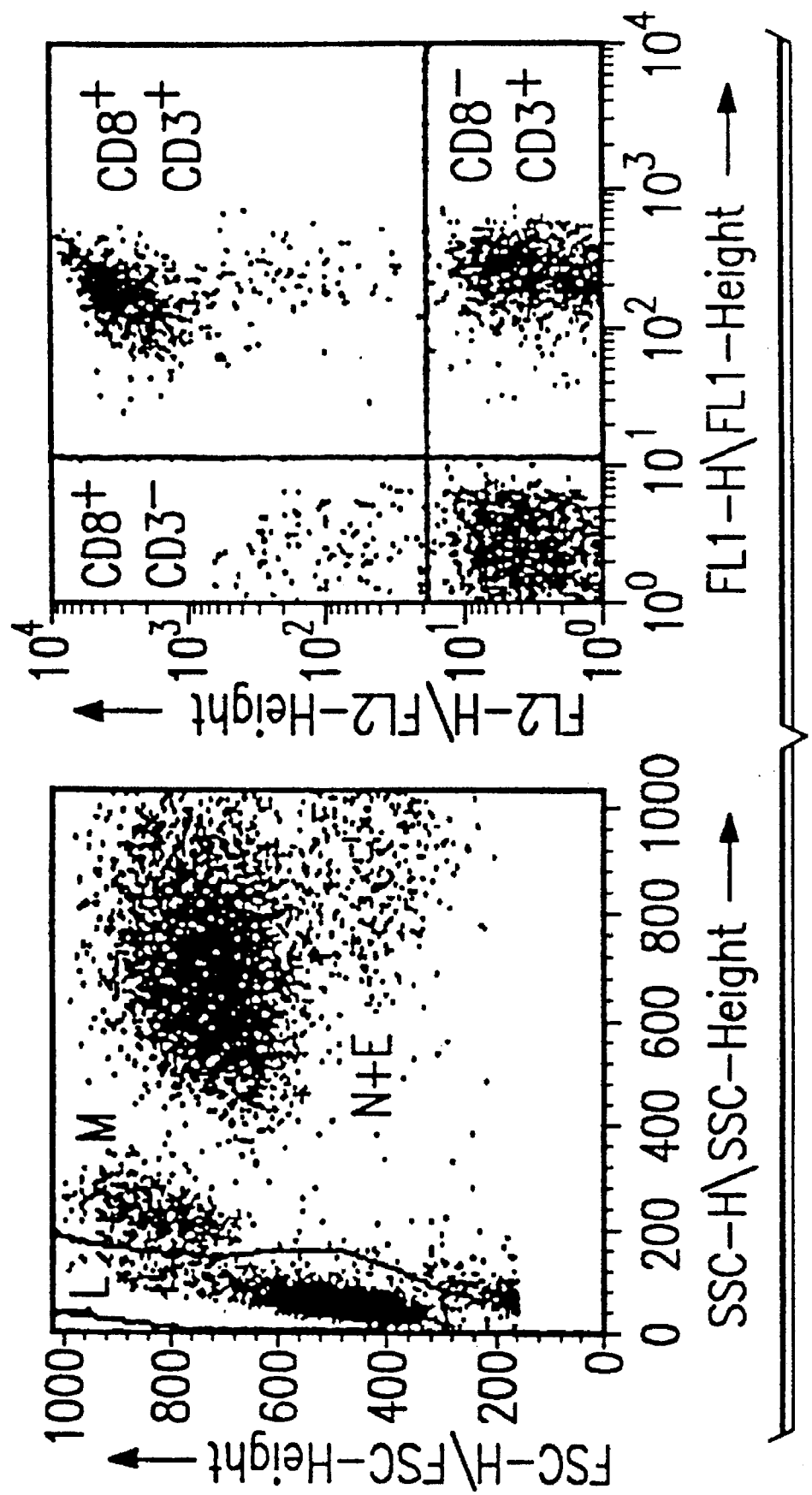

FIGS. 4a through 4d show a FACScan™ displays of a normal blood sample processed as described in Examples 2, 3 and 4. FIG. 4a was processed without the addition of any antibody as a negative control of the donor sample; FIG. 4b was processed as described in Example 4 to identify pan B cells (CD19+lymphocytes) and pan T cells (CD3+ lymphocytes). The lymphocyte population was gated first on the Forward Scatter (FSC) vs Side Scatter (SSC) plot and reanalyzed in the Green Fluorescence (FL1) vs Orange Fluorescence (FL2) channels. As can be seen in FIGS. 4a through 4d unlabeled lymphocytes were all in the lower left quadrant, while the CD3-FITC antibody labeled Pan T cells moved out to the lower right quadrant and the CD19-PE labeled Pan B cells moved up to the upper left quadrant. FIG. 4c sample was processed as described in Example 2 to identify Helper T cells (CD4+lymphocytes). Helper T cells are a subpopulation of T lymphocytes and have both CD3 and CD4 antigens on the cell surface and therefore they moved out to the right because of the FITC label on the anti-CD3 antibody and moved up to the upper right quadrant because of the PE label on the anti-CD4 antibody. FIG. 4d sample was processed as described in Example 3 to identify suppressor T cells (CD8+lymphocytes). Suppressor T cells are also a subpopulation of T lymphocytes and have both CD3 and CD8 antigens. Therefore the cells were labeled with both antibody and fell into the upper right quadrant.

FIGS. 5b, 5d, 5f and 5h represent FACScan™ display printouts of a normal blood sample processed as described in Examples 2, 3 and 4. FIGS. 5a, 5c, 5e and 5g represent the same sample processed as described in the same examples above, except that the red cells were lysed with a commercial lysing solution, Becton Dickinson's FacsLyse™ as described in Example 11. Columns 1 and 3 are FSC vs SSC cytograms and columns 2 and 4 are FL1 vs FL2 two dimensional dot plots of the gated lymphocytes. The same FSC, SSC, FL1 and FL2 gains were used for the analysis of both samples for comparison.

As can be seen in the FSC vs SSC cytograms, the right column cytograms show well defined clusters of neutrophils, eosinophils, monocytes and lymphocytes, which are all well separated from noise (the signals mostly from red cell stroma), indicating that the white cells were well preserved in the multi-purpose blood diluent. This allows more accurate lymphocyte gating. In comparison, the cell clusters of the left column cytograms are less well defined. The resolution of each cell cluster is less clear and the signals of the granulocytes are much lower than that of the right column, suggesting an alteration in the refractive index of these cells which may have resulted from the leakage of some protein components. The quality of the FL1 vs FL2 two dimensional dot plots of the gated lymphocytes of the last column is essentially equivalent to that of the corresponding dot plot of the second column whose red cells were lysed with FacsLyse™.

Figure 5A:
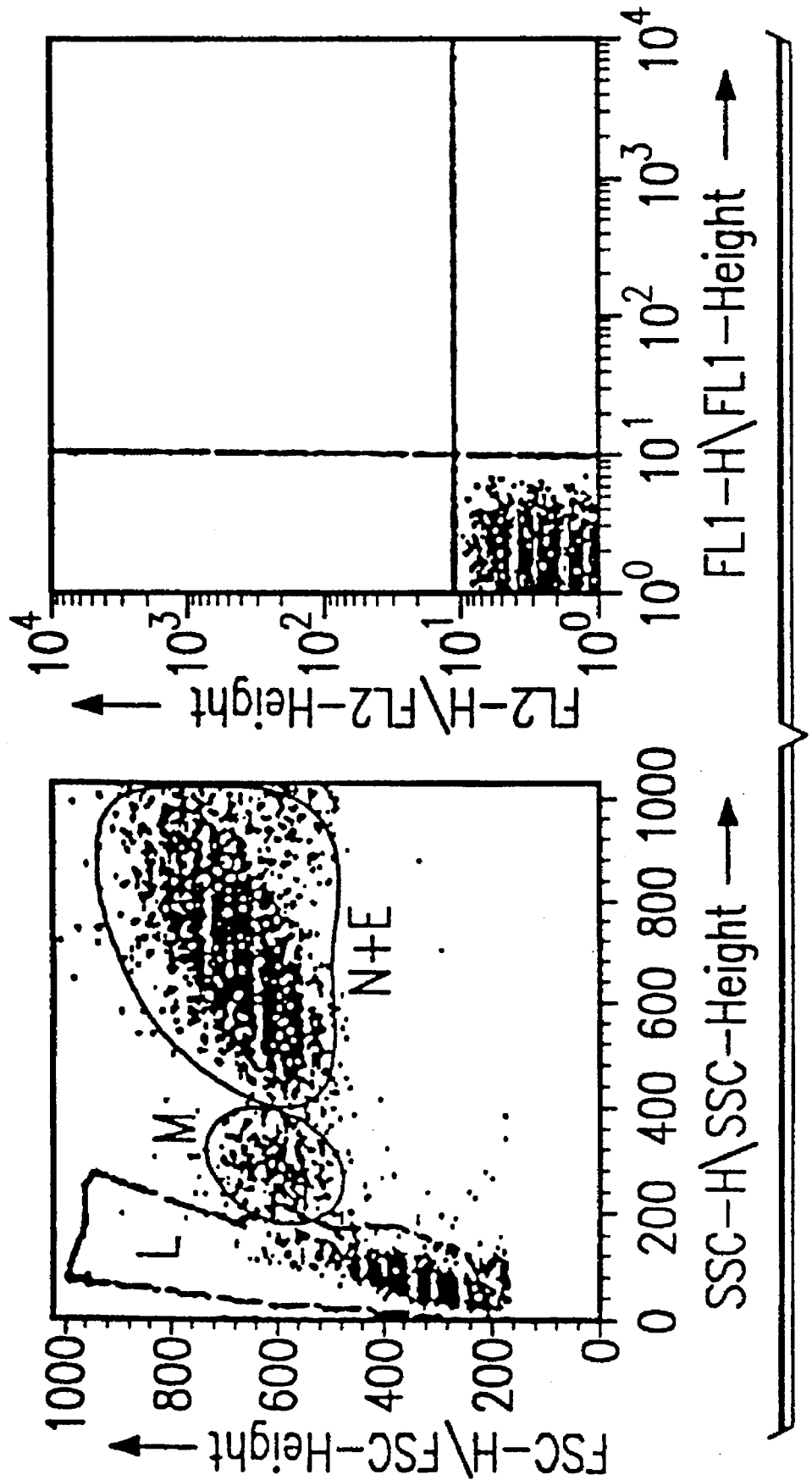
FIGS. 5a, 5c, 5e and 5g show FACScan™ display printouts of the same sample prepared in the same way but lysed with Becton Dickinson's FacsLyse™.
Figure 5B:
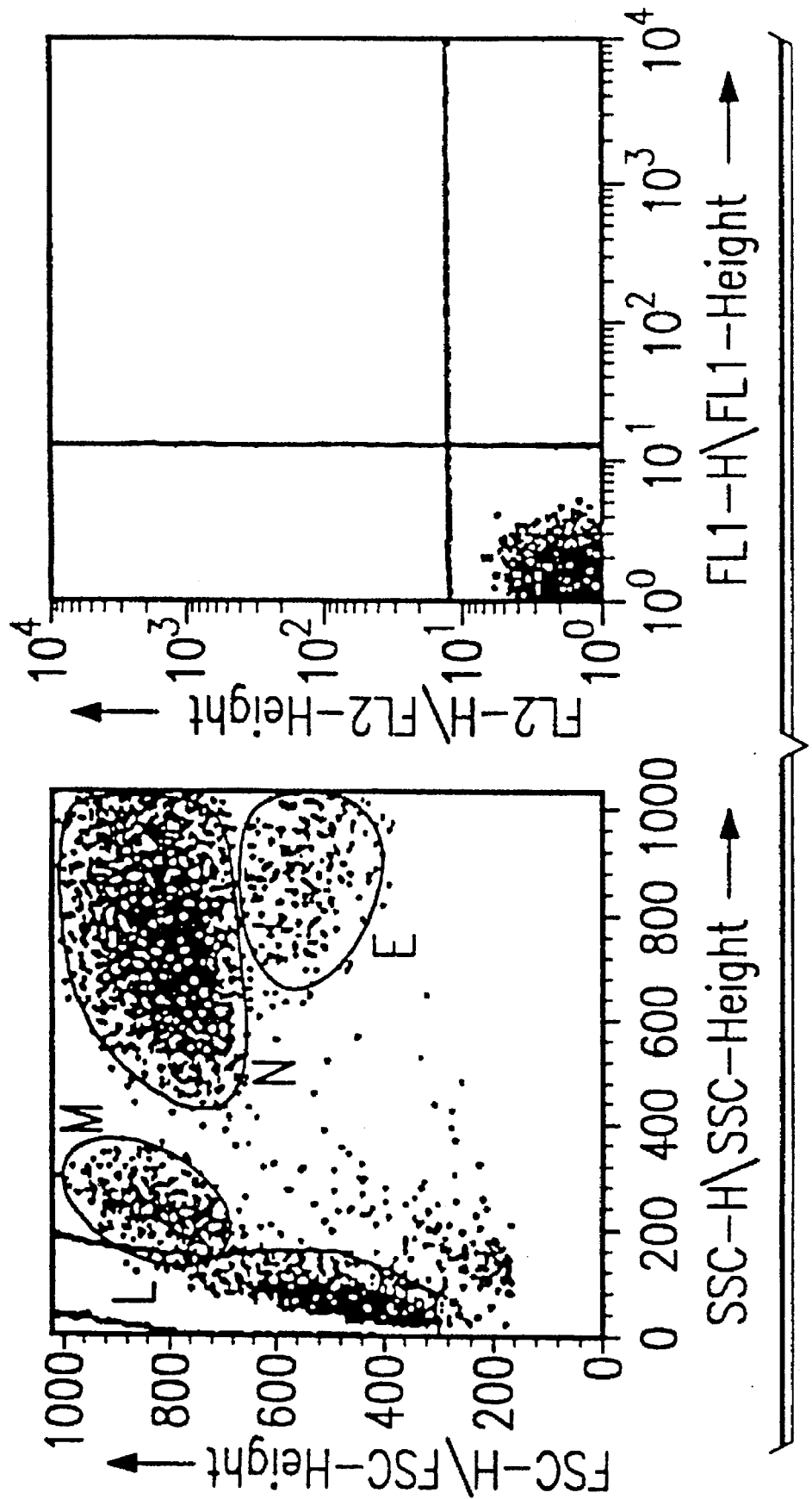
FIGS. 5b, 5d, 5f and 5h show FACScan™ display printouts of a normal blood sample processed as described in Examples 2, 3 and 4 for immuno-phenotyping
Figure 5C:
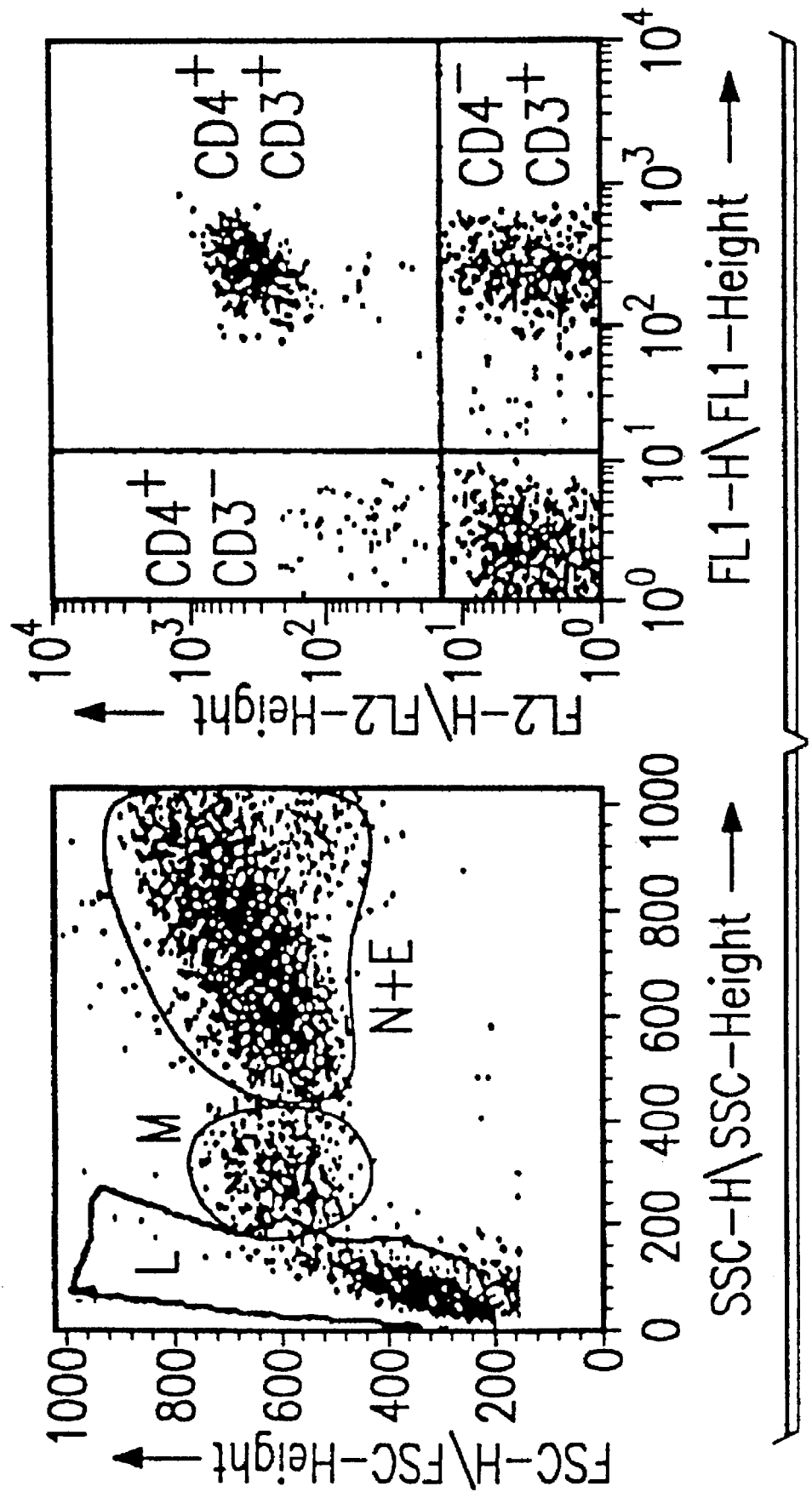
Figure 5D:
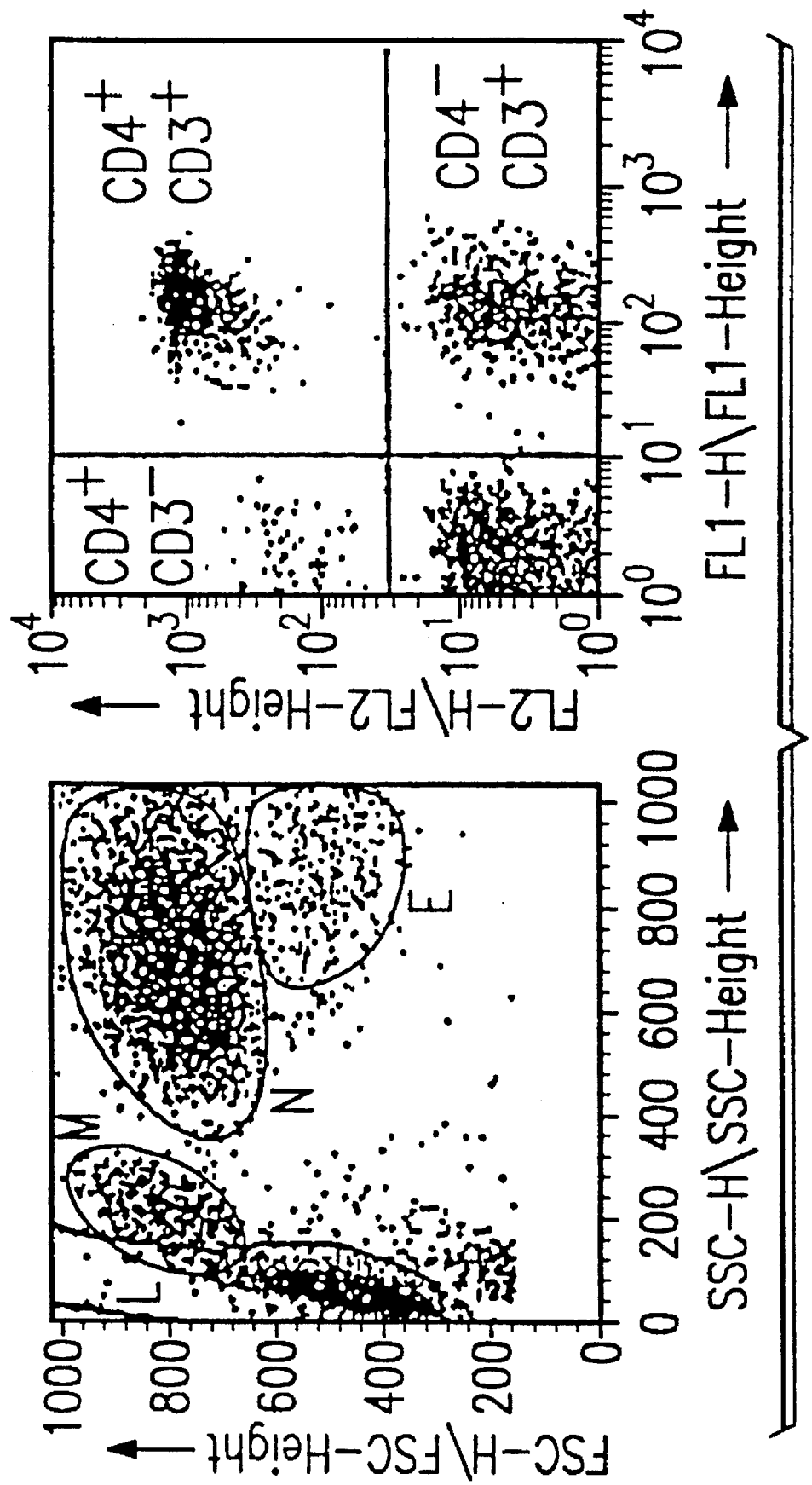
Figure 5E:
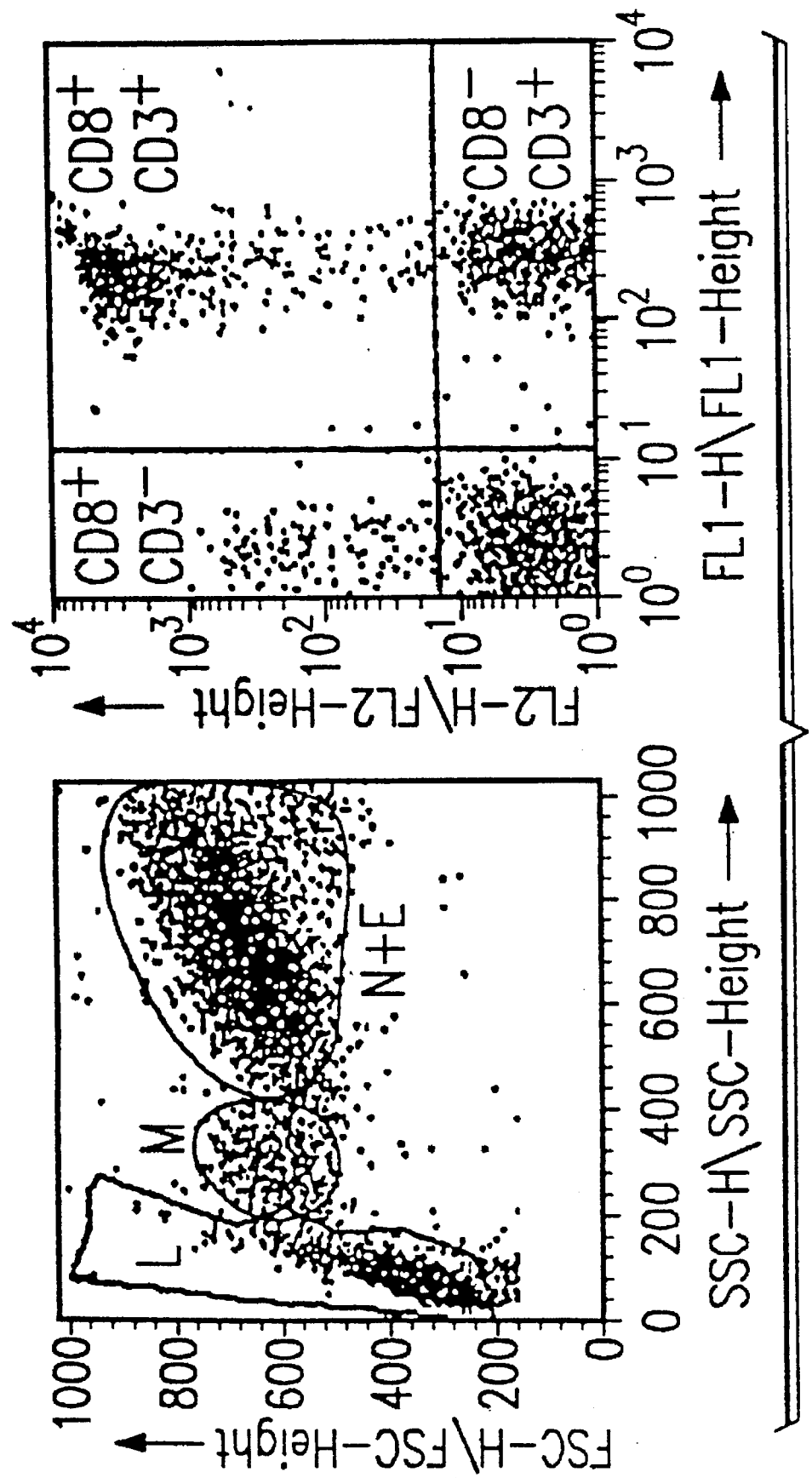
Figure 5F:
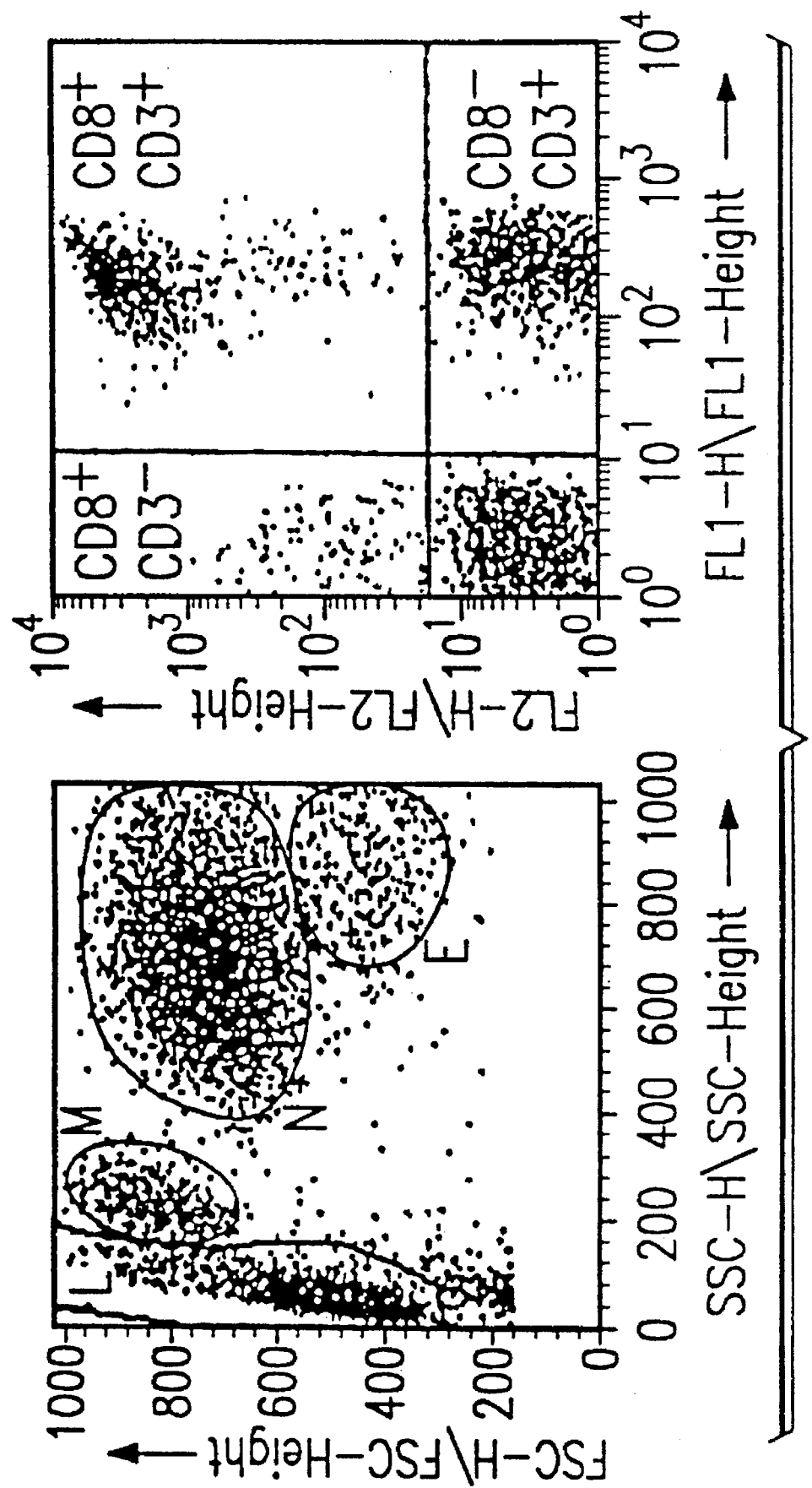
Figure 5G:
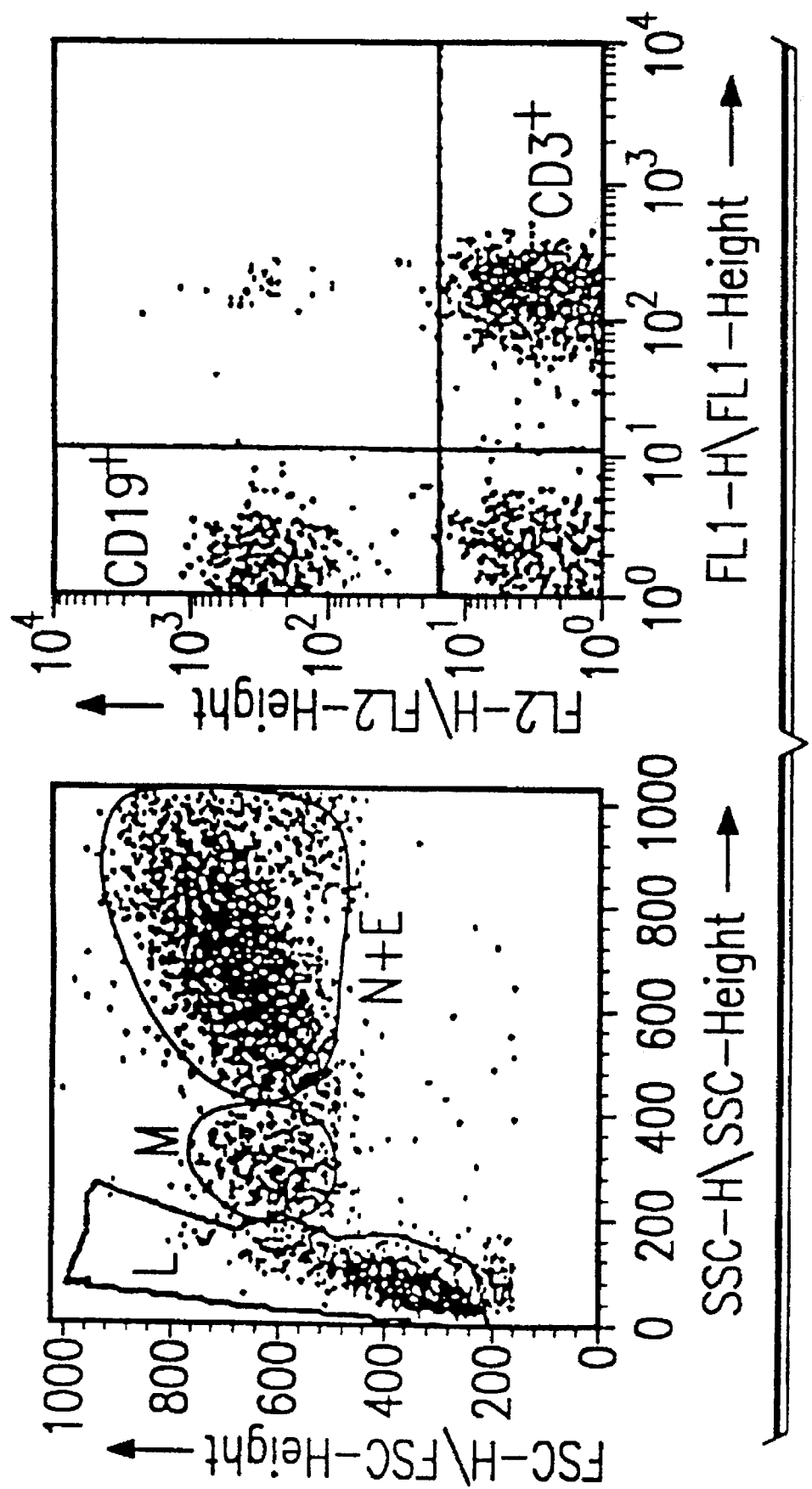
Figure 5H:
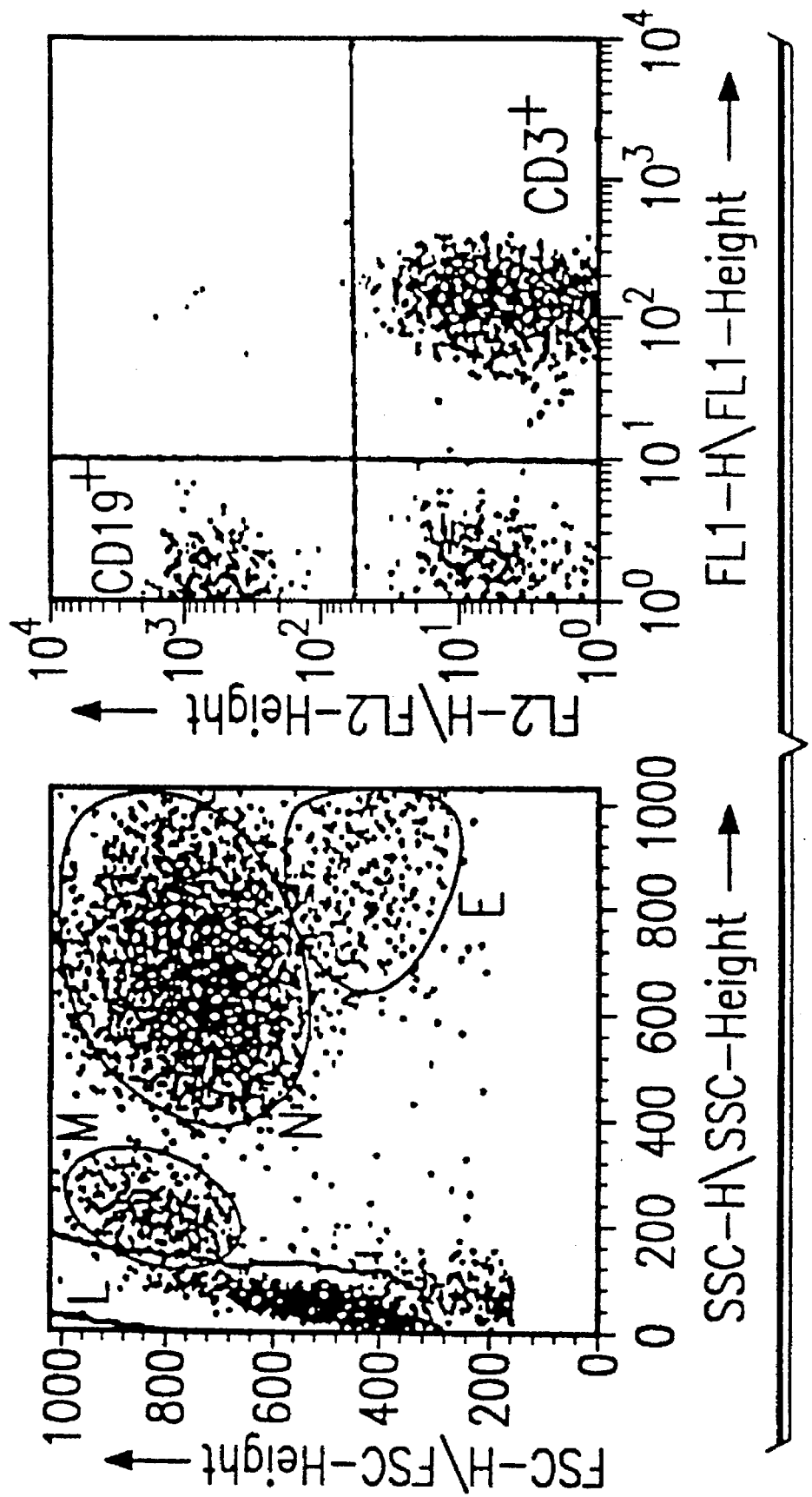

FIG. 5a is a negative control of a normal blood, processed as described in Example 2 but not reacted with any antibody, lysed with FacsLyse™; FIG. 5b is also a negative control of the same sample but red cells were lysed with the multipurpose diluent of one embodiment of the present invention. FIGS. 5c, e and g represent the same sample processed as described in Examples 2, 3 and 4 but red cells were lysed with FacsLyse™ as described in Example 1. FIGS. 5d, f and h are the same sample processed as described Examples 2, 3 and 4 in which red cells were lysed with the multipurpose diluent of one embodiment of the present invention.

The invention is further defined by reference to the following examples, which are intended to be illustrative and not limiting.

EXAMPLE 1

WHITE BLOOD CELL DIFFERENTIAL ANALYSIS

Fifty microliters of an EDTA-anti-coagulated normal blood sample was mixed with 1 ml of the multipurpose reagent system prewarmed at 40° C., mixed and incubated at room temperature for 16 seconds. The reagent system contained 0.5% weight/volume ammonium chloride, 0.08% weight/volume of formaldehyde, 0.01% weight/volume of saponin, 0.1% weight/volume of potassium bicarbonate, and 20 mM of acetate buffer. The reagent system had a pH of about 6.2 and an osmolality of 267 mOsm/L. This mixture was incubated at 38±2° C. for 16 seconds and run on the CD3500™ system directly through the optical system bypassing the system hydraulics. The cytograms of the sample are presented in FIG. 1.

EXAMPLE 2

LYMPHOCYTE IMMUNOPHENOTYPING

Fifty microliters of EDTA-anti-coagulated whole blood was mixed with 10 microliters of monoclonal antibody solution containing anti-CD3-FITC and anti-CD4-PE in a test tube.

The mixture was incubated at room temperature for 15 minutes before adding 1.0 milliliter of the multipurpose reagent system of the present invention containing 0.5% weight/volume of ammonium chloride, 0.02% of weight/volume of tetra sodium EDTA, 0.1% of volume of formaldehyde, 0.0075% weight/volume of saponin, 0.01% weight/volume of potassium bicarbonate, and 20 mM acetate buffer. The reagent system had a pH of about 6.2 and an osmolality of 270 mOsm per liter, while the reagent system-blood solution had a pH around 7.0.

The reagent system-blood solution was incubated from 20 seconds to 10 minutes at room temperature. This variation in acceptable incubation time allowed for the analysis of multiple samples.

The percent of CD3+ and CD4+ lymphocyte subpopulations was determined on the FACScan™ flow cytometer as illustrated in FIG. 4a.

EXAMPLE 3

LYMPHOCYTE IMMUNOPHENOTYPING

Fifty microliters of EDTA-anti-coagulated whole blood was mixed with 10 microliters of monoclonal antibody solution containing anti-CD3-FITC and anti-CD8-PE in a test tube.

The mixture was incubated at room temperature for 15 minutes before adding 1.0 milliliter of the multipurpose reagent system of the present invention containing 0.5% weight/volume of ammonium chloride, 0.02% weight/volume of tetra sodium EDTA, 0.1% of volume of formaldehyde, 0.0075% weight/volume of saponin, 0.01% weight/volume of potassium bicarbonate, and 20 mM acetate buffer. The reagent system, described in EXAMPLE 1, had a pH of about 6.2 and an osmolality of 270 mOsm per liter.

The whole blood-reagent system solution could be incubated anywhere from 20 seconds to 10 minutes at room temperature, which allowed for the analysis of multiple samples.

The percent of CD3+ and CD8+ lymphocyte subpopulations were determined using the FACScan™ flow cytometer.

EXAMPLE 4

LYMPHOCYTE IMMUNOPHENOTYPING

Fifty microliters of EDTA-anti-coagulated whole blood was mixed with 10 microliters of monoclonal antibody solution containing anti-CD3-FITC and anti-CD19-PE in a test tube.

The mixture was incubated at room temperature for 15 minutes before adding 1.0 milliliter of a multipurpose reagent system of the present invention containing 0.5% weight/volume of ammonium chloride, 0.02% weight/volume of tetra sodium EDTA, 0.1% volume of formaldehyde, 0.0075% weight/volume of saponin, 0.01% weight/volume of potassium bicarbonate, and 20 mM acetate buffer. The multipurpose reagent system, as described in EXAMPLE 1, had a pH of about 6.2, and an osmolality of 270 mOsm per liter.

The whole blood-reagent system solution could be incubated from 20 seconds to 10 minutes at room temperature. This variation in incubation time permits the analysis of multiple samples.

The percent of CD3+ and CD19+ lymphocyte subpopulations were determined using a FACScan™ flow cytometer as illustrated in FIG. 4b.

EXAMPLE 5

NUCLEATED RED BLOOD CELL DETERMINATION

Fifty microliters of an EDTA-anti-coagulated whole blood samples with and without chicken nuclei were mixed with 950 microliters of the multipurpose reagent system of the present invention containing 0.1 mg % weight/volume of a nuclear stain, 0.5% weight/volume of ammonium chloride, 0.075% of volume of formaldehyde, 0.01% weight/volume of saponin, 0.01% weight/volume of potassium bicarbonate, and 20 mM acetate buffer. The multipurpose reagent system had a pH of about 6.0 and an osmolality of 270 mOsm per liter.

The whole blood-reagent system solution was incubated at 38±2° C. for 20 seconds.

The percentage of nucleated red blood cells in the whole blood sample was determined on a FACScan™ flow cytometer as illustrated in FIG. 3.

EXAMPLE 6

WHITE BLOOD CELL DIFFERENTIAL ANALYSIS

Fifty microliters of EDTA-anti-coagulated whole blood was mixed with 950 microliters of the multipurpose reagent system of the present invention containing 20 mM MES buffer, 0.5% weight/volume of ammonium fluoride, 0.08% of volume of formaldehyde, and 0.01% weight/volume of saponin. The reagent system had a pH of about 6.2 and an osmolality of 280 mOsm per liter.

The whole blood-reagent system solution was incubated at 40° C. for 20 seconds.

A differential analysis of the white blood cells was performed on an experimental clinical flow cytometer.

EXAMPLE 7

WHITE BLOOD CELL DIFFERENTIAL ANALYSIS

Fifty microliters of EDTA-anti-coagulated whole blood was mixed with 1.0 milliliter of the multipurpose reagent system of the present invention containing 20 mM MOPS buffer, 0.5% weight/volume of ammonium chloride, 0.1% of volume of formaldehyde, 0.012% weight/volume of saponin and 0.01% weight/volume of tetrasodium EDTA. The multipurpose reagent system had a pH of about 7.0 and an osmolality of 280 mOsm per liter.

The whole blood-reagent system solution was incubated at 42° C. for 20 seconds.

A differential analysis of the white blood cells was performed on an experimental clinical flow cytometer.

EXAMPLE 8

WHITE BLOOD CELL DIFFERENTIAL ANALYSIS

Fifty microliters of EDTA-anti-coagulated whole blood was mixed with 1.0 milliliter of the multipurpose reagent system of the present invention containing 20 mM HEPES buffer, 0.4% weight/volume of ammonium fluoride, 0.08% of volume of formaldehyde, 0.01% weight/volume of saponin, and 0.1% weight/volume of potassium bicarbonate. The reagent system had a pH of about 7.0 and an osmolality of 270 mOsm per liter.

The whole blood-reagent system solution was mixed at 40° C. for about 20 seconds.

A differential analysis of the white blood cells was performed on an experimental clinical flow cytometer.

EXAMPLE 9

DIFFERENTIAL INCUBATION TIMES FOR WHITE BLOOD CELL DETERMINATIONS

Fifty microliters of EDTA-anti-coagulated whole blood was mixed with 950 microliters of the multipurpose reagent system of the present invention at 38±2° C. The reagent system contained 0.5% weight/volume of ammonium chloride, 0.08% of volume of formaldehyde, 0.01% weight/volume of saponin, 0.01% weight/volume of potassium bicarbonate, and 20 mM acetate buffer. The reagent system had a pH of about 6.2 and an osmolality of 267 mOsm per liter.

The mixture was incubated at 38±2° C. and serial aliquots of the mixture were removed at 14 seconds, 2 minutes, 4 minutes, 6 minutes, 8 minutes, and 10 minutes.

A five-part differential analysis of the white blood cells was performed on each aliquot on an experimental clinical flow cytometer equipped with an argon-ion laser.

EXAMPLE 10

VARIATIONS IN INCUBATION TIME AND TEMPERATURE FOR WHITE BLOOD CELL DETERMINATIONS

Fifty microliters of EDTA-anti-coagulated whole blood was mixed with 950 microliters of the multipurpose reagent system of the present invention containing 0.5% weight/volume of ammonium chloride, 0.08% of volume of formaldehyde, 0.01% weight/volume of saponin, 0.01% weight/volume of potassium bicarbonate, and 20 mM acetate buffer. The reagent system had a pH of about 6.2 and an osmolality of 267 mOsm/L.

Aliquots of the resultant mixture were incubated at 36° C., 38° C., 40° C., 42° C., 45° C., and 46° C. respectively for various time intervals up to 10 minutes.

A five-part white cell differential analysis was determined on samples of each aliquot using an automated electrical optical system.

EXAMPLE 11

COMPARATIVE STUDIES OF A COMMERCIAL LYSING SOLUTION AND THE MULTIPURPOSE REAGENT SYSTEM OF THE PRESENT INVENTION

A commercial lysing solution from Becton Dickinson (FacsLyse™) was compared with one embodiment of the multipurpose reagent system of the present invention (the "Multipurpose Diluent") in an immuno-phenotyping experiment. The samples were processed as described in Examples 2, 3, and 4 and the results are presented in TABLE 1.

In the case the commercial FacsLyse™, the mixture of the test sample and the FacsLyse™ was first incubated in the dark at room temperature for 10 minutes. Afterward, the resulting mixture was centrifuged for 5 minutes at 3000 g. The supernatant was separated and the cell button was then washed with 1 ml of phosphate buffered saline. The cell suspension was again centrifuged for 5 minutes at 3000 g. Afterward, the cell button was resuspended in a phosphate buffered saline containing 1% by weight of paraformaldehyde. The assay was then performed on a FACScan™.

In contrast to the elaborate and lengthy red cell lysing procedure as described above, in the case of one embodiment of the multipurpose reagent system of the present invention (the "Multipurpose Diluent"), the entire assay procedure was completed in about 20 seconds. No washing step was required.

The comparative data are compiled in TABLE 1. As can be seen from this TABLE, the results obtained from the procedure using a commercial lysing solution and those obtained from the procedure using the multipurpose reagent system of the present invention are essentially equivalent.

EXAMPLE 12

WHITE BLOOD CELL DIFFERENTIAL ANALYSIS

Fifty microliters of an EDTA-anti-coagulated normal blood sample was mixed with 1 ml of the multipurpose reagent system prewarmed at 40° C., mixed and incubated at room temperature for 16 seconds. The reagent system contained 0.5% weight/volume of ammonium chloride, 0.08% volume of formaldehyde, 0.01% weight/volume of saponin, 0.1% weight/volume of potassium bicarbonate, and 10 mM of acetate buffer. The reagent system had a pH of about 6.2 and an osmolarity of 225 mOsm/L. This mixture was incubated at 38±2° C. for 16 seconds and run on the CD3500™ analyzer system directly through the optical system but bypassing the system hydraulics. The cytograms of the sample are presented in FIG. 2.

Although the present invention and its advantages have been described in detail, it should be appreciated by those skilled in the art that the conception and the specific embodiments disclosed may be readily utilized as a basis for modifying or designing other systems or reagents for carrying out the same purposes of the present invention. It should also be realized by those skilled in the art that such equivalent constructions do not depart from the spirit and scope of the invention as set forth in the appended claims.

TABLE 1

COMPARISON OF LYMPHOCYTE SUB-TYPING RESULTS
FACS LYSE ™ vs MULTIPURPOSE BLOOD DILUENT DISCLOSED

| Type of Mab. used for Immunophenotyping | Donor No. | Labled Population | FacsLyse % labeled | Multipurpose Diluent % labeled |
|---|---|---|---|---|
| CD3FITC/CD4PE | No. 1 | CD3 − CD4 + | 1.36 | 1.75 |
| | | CD3 + CD4 + | 32.66 | 31.84 |
| | | CD3 + CD4 − | 35.14 | 37.43 |
| | | CD3 − CD3 + | 30.84 | 28.98 |
| CD3FITC/CD8PE | No. 1 | CD3 − CD8 + | 3.94 | 3.53 |
| | | CD3 + CD8 + | 23.54 | 27.26 |
| | | CD3 − CD8 − | 34.19 | 37.40 |
| | | CD3 + CD8 − | 34.61 | 35.52 |
| CD3FITC/CD19PE | No. 1 | CD3 − CD19 + | 24.77 | 26.41 |
| | | CD3 + CD19 + | 1.16 | 0.20 |
| | | CD3 − CD19 − | 12.53 | 10.36 |
| | | CD3 + CD19 − | 61.54 | 63.03 |
| CD3FITC/CD4PE | No. 2 | CD3 − CD4 + | 2.59 | 3.45 |
| | | CD3 + CD4 + | 46.66 | 45.86 |
| | | CD3 − CD4 − | 24.90 | 25.73 |
| | | CD3 + CD4 − | 25.02 | 25.80 |
| CD3FITC/CD8PE | No 2 | CD3 − CD8 + | 7.99 | 7.80 |
| | | CD3 + CD8 + | 24.52 | 24.95 |
| | | CD3 − CD8 − | 24.17 | 23.40 |
| | | CD3 + CD8 + | 43.32 | 43.85 |
| CD3FITC/CD19PE | No. 2 | CD3 − CD19 + | 9.83 | 9.85 |
| | | CD3 + CD19 + | 0.35 | 0.00 |
| | | CD3 − CD19 − | 20.94 | 18.61 |
| | | CD3 + CD19 − | 68.88 | 71.54 |

What is claimed is:

1. A method for the rapid analysis of nucleated peripheral blood cells from a whole blood comprising the steps of:

forming a mixture by mixing whole blood and a multipurpose reagent system in the ratio of about 1 part to a range of from about 16 to about 100 parts, wherein said reagent system is suitable for the automated, multi-part differentiation of white blood cells (WBC), WBC immunophenotyping and the detection of nucleated red blood cells, said multipurpose reagent system concurrently lysing red blood cells and fixing white blood cells in a whole blood sample while preserving WBC membranes and surface antigens, said reagent system comprises from about 3 to about 7 gm/L of a non-quaternary ammonium salt, from about 0.04 to about 0.1 percent by volume of a $C_1$-$C_4$ aliphatic aldehyde, from about 10 to about 20 mM of a non-phosphate buffer, said non-phosphate buffer being characterized as substantially inert to said aliphatic aldehyde, and water, such that said multi-purpose reagent system is maintained at a pH between about 5.5 to about 7.5 and an osmolality between about 160 to about 310 mOsm per liter;

incubating the mixture at temperatures from about 25° C. to about 46° C. for at least about 10 seconds; and determining the nucleated peripheral blood cells with an automated electro-optical hematology instrumentation.

2. The method as recited in claim 1, further comprising the step of adding antibodies that are directed against cell surface markers to the whole blood prior to mixing the whole blood and the multi-purpose reagent.

3. The method as recited in claim 2, wherein said antibodies are conjugated to flourochromes.

4. The method as recited in claim 2, wherein said antibodies comprise monoclonal antibodies.

5. The method as recited in claim 2, wherein said antibodies are directed to lymphocyte surface antigens.

6. The method as recited in claim 1, wherein the determination of nucleated peripheral blood cells comprises lymphocyte immunophenotyping wherein monoclonal antibodies conjugated to fluorochromes are added to the whole blood prior to mixing the whole blood and the multipurpose reagent.

7. The method as recited in claim 1, wherein the determination of nucleated peripheral blood cells comprises the determination of at least five classes of leukocytes.

8. The method as recited in claim 1, wherein the determination of nucleated peripheral blood cells comprises the determination of nucleated erythrocytes.

9. The method of claim 1, wherein the multipurpose reagent system further comprises from about 0.05 mg % to about 0.15 mg % by weight volume of nuclear stain.

10. The method of claim 1, wherein the multipurpose reagent system further comprises about 0.1 mg % by weight volume of nuclear stain.

* * * * *

UNITED STATES PATENT AND TRADEMARK OFFICE
CERTIFICATE OF CORRECTION

PATENT NO. : 5,648,225
DATED : July 15, 1997
INVENTOR(S) : Kim et al.

It is certified that error appears in the above-identified patent and that said Letters Patent is hereby corrected as shown below:

In the title, line 2, change "BEAGENT" to --REAGENT--.

Signed and Sealed this

Sixteenth Day of December, 1997

Attest:

BRUCE LEHMAN

*Attesting Officer*  *Commissioner of Patents and Trademarks*